US010513487B2

(12) United States Patent
Knauf et al.

(10) Patent No.: US 10,513,487 B2
(45) Date of Patent: *Dec. 24, 2019

(54) METHODS FOR PRODUCING CHEMICAL PRODUCTS WITH OPERATION INTERRUPTIONS

(71) Applicant: Covestro Deutschland AG, Leverkusen (DE)

(72) Inventors: Thomas Knauf, Dormagen (DE); Peter Drinda, Krefeld (DE); Stefan Wershofen, Mönchengladbach (DE); Klaus-Gerd Gruner, Duisburg (DE); Volker Hartjes, Duisburg (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/320,807

(22) PCT Filed: Jun. 22, 2015

(86) PCT No.: PCT/EP2015/063926
§ 371 (c)(1),
(2) Date: Dec. 21, 2016

(87) PCT Pub. No.: WO2015/197522
PCT Pub. Date: Dec. 30, 2015

(65) Prior Publication Data
US 2017/0152210 A1 Jun. 1, 2017

(30) Foreign Application Priority Data
Jun. 24, 2014 (EP) .................................... 14173585

(51) Int. Cl.
C07C 201/08 (2006.01)
C07C 205/06 (2006.01)
B01J 19/24 (2006.01)
C07C 201/16 (2006.01)

(52) U.S. Cl.
CPC ............ *C07C 201/08* (2013.01); *B01J 19/24* (2013.01); *C07C 201/16* (2013.01); *C07C 205/06* (2013.01); *B01J 2208/00637* (2013.01); *B01J 2208/00646* (2013.01); *B01J 2208/00716* (2013.01); *B01J 2219/00033* (2013.01); *B01J 2219/24* (2013.01)

(58) Field of Classification Search
CPC ... C07C 201/08; C07C 201/16; C07C 205/06; B01J 19/24; B01J 2208/00637; B01J 2208/00646; B01J 2208/00716; B01J 2219/00033; B01J 2219/24
See application file for complete search history.

(56) References Cited

U.S. PATENT DOCUMENTS

| | | | |
|---|---|---|---|
| 2,256,999 A | 9/1941 | Castner | |
| 3,544,611 A * | 12/1970 | Alheritiere | C07C 263/10 203/78 |
| 4,265,834 A | 5/1981 | Birkenstock et al. | |
| 4,772,757 A | 9/1988 | Lailach et al. | |
| 4,847,408 A | 7/1989 | Frosch et al. | |
| 4,851,570 A | 7/1989 | Zaby et al. | |
| 5,013,811 A * | 5/1991 | Ross | C08G 18/12 528/59 |
| 5,053,539 A | 10/1991 | Yano et al. | |
| 5,077,371 A * | 12/1991 | Singh | C08G 18/12 528/64 |
| 5,117,048 A | 5/1992 | Zaby et al. | |
| 5,136,087 A | 8/1992 | Van Horn et al. | |
| 5,286,760 A | 2/1994 | Bolton et al. | |
| 5,449,818 A | 9/1995 | Biskup et al. | |
| 5,763,697 A | 6/1998 | Hermann et al. | |
| 5,808,157 A | 9/1998 | Langer et al. | |

(Continued)

FOREIGN PATENT DOCUMENTS

DE 1133394 7/1962
EP 0436443 A2 7/1991
(Continued)

OTHER PUBLICATIONS

Tham et al. (Distillation, 2 pages, published Jul. 2009) (Year: 2009).*
Wegener, G. et al; Applied Catalysis A: General 221 (2001); "Trends in industrial catalysis in the polyurethane industry"; pp. 303-335; Elsevier Science B.V; Dormagen, Germany.
Siefken, Von Werner; Justus Liebigs Annalen Der Chemie; 562. Band; (Dec. 11, 1948) Mono- und Polyisocyanate IV. Mitteilung über Polyurethane); pp. 75-106; Leverkusen, Germany.
Ullmanns Encyklopädie der technischen Chemie; Band 13; 4th edition; (1977); Hormone bis Keramik; pp. 351-353; Verlag Chemie Weinheim/New York.

(Continued)

*Primary Examiner* — Yevgeny Valenrod
*Assistant Examiner* — Blaine G Doletski
(74) *Attorney, Agent, or Firm* — N. Denise Brown

(57) ABSTRACT

This invention relates to methods for producing chemical products, wherein the one or more feed materials are reacted to form a chemical product or a chemical composition. The invention further relates to plants for performing such methods, said plants being designed in such a way that, during an interruption of the methods, no input of at least one feed material into the reaction occurs and the plant parts not affected by a revision measure, maintenance measure, repair measure, or cleaning measure are operated in so-called re-circulation mode. It is thereby achieved, among other things, that only the affected plant part needs to be shut down for the time of the measure, which can be advantageous with regard to the productivity and economy of the method and the quality of the produced products. Finally, the invention relates to methods for operating plants in the event that individual plant parts are taken out of service.

9 Claims, 2 Drawing Sheets

(56) References Cited

U.S. PATENT DOCUMENTS

| | | | |
|---|---|---|---|
| 5,877,350 | A | 3/1999 | Langer et al. |
| 6,043,394 | A | 3/2000 | Langer et al. |
| 6,562,247 | B2 | 5/2003 | Gillis et al. |
| 6,803,483 | B2 | 10/2004 | Lokum et al. |
| 7,108,770 | B2 | 9/2006 | Grün et al. |
| 7,118,653 | B2 | 10/2006 | Brady et al. |
| 7,230,130 | B2 | 6/2007 | Ströfer et al. |
| 7,253,321 | B2 | 8/2007 | Hagen et al. |
| 7,521,576 | B2 | 4/2009 | Schal et al. |
| 7,541,487 | B2 | 6/2009 | Pohl et al. |
| 7,547,801 | B2 | 6/2009 | Pohl et al. |
| 7,615,662 | B2 | 11/2009 | Pohl et al. |
| 7,649,108 | B2 | 1/2010 | Schal et al. |
| 8,044,244 | B2 | 10/2011 | Seidemann et al. |
| 8,097,751 | B2 | 1/2012 | Koch et al. |
| 9,024,057 | B2 | 5/2015 | Biskup et al. |
| 9,067,864 | B2 | 6/2015 | Sommer et al. |
| 9,150,493 | B2 | 10/2015 | Lorenz et al. |
| 9,260,377 | B2 | 2/2016 | Knauf et al. |
| 9,284,256 | B2 | 3/2016 | Knauf et al. |
| 9,290,438 | B2 | 3/2016 | Merkel et al. |
| 9,421,509 | B2 | 8/2016 | Arai |
| 9,469,594 | B2 | 10/2016 | Merkel et al. |
| 9,593,075 | B2 | 3/2017 | Bruns et al. |
| 2005/0227129 | A1 | 10/2005 | Iio |
| 2006/0089507 | A1* | 4/2006 | Sohn ............... C07C 263/10 560/347 |
| 2008/0262112 | A1* | 10/2008 | Marion ............. B01J 8/22 518/706 |
| 2009/0281350 | A1* | 11/2009 | Knoesche .......... C07C 263/10 560/347 |
| 2010/0298596 | A1 | 11/2010 | Keggenhoff et al. |
| 2012/0095255 | A1* | 4/2012 | Mattke ............. C07C 263/10 560/347 |
| 2012/0123152 | A1* | 5/2012 | Bruns .............. C07C 263/10 560/347 |
| 2013/0060062 | A1* | 3/2013 | Mattke ............. C07C 263/10 560/347 |
| 2014/0039648 | A1* | 2/2014 | Boult .............. G05B 15/02 700/79 |

FOREIGN PATENT DOCUMENTS

| | | |
|---|---|---|
| GB | 913444 | 12/1962 |
| GB | 1452466 | 10/1976 |
| WO | 2006125759 A1 | 11/2006 |
| WO | 2013053371 | 4/2013 |

OTHER PUBLICATIONS

Ullmanns Encyklopädie der technischen Chemie; 4th edition; vol. 17; p. 391; (1979); Verlag Chemie Weinheim/New York.

Hermann, H. et al; ACS Symposium Series; American Chemical Society: Washington, D.C. (1996); "Industrial Nitration of Toluene to Dinitrotoluene Requirements of a Modern Facility for the Production of Dinitrotoluene"; L.F. Albright, R.V. C Carr, R. J. Schmitt; pp. 234-249; Series 623; Cologne, Germany.

* cited by examiner

METHODS FOR PRODUCING CHEMICAL PRODUCTS WITH OPERATION INTERRUPTIONS

CROSS-REFERENCE TO RELATED APPLICATIONS

This Application is a national stage application under 35 U.S.C. § 371 of PCT/EP2015/063926, filed Jun. 22, 2015, which claims the benefit of European Application No. 14173585.2, filed Jun. 24, 2014, both of which are incorporated by reference herein.

FIELD

The present invention relates to processes for preparing chemical products in which the feedstock(s) is/are converted to a chemical product or a chemical composition. The present invention further relates to plants for performing such processes, which are configured such that, during an interruption of the processes, no introduction of at least one feedstock into the reaction takes place and the plant sections unaffected by an inspection, maintenance, repair or cleaning measure are operated in circulation mode. What this achieves, among other effects, is that only the plant section in question needs to be shut down for the period of the measure, which may be advantageous in terms of productivity and economic viability of the process and the quality of the products prepared. Finally, the invention provides methods of operating plants in the event of shutdown of individual plant sections.

BACKGROUND

Chemical processes on the industrial scale are available for production of chemical intermediates and end products. The processes can be operated batchwise, semicontinuously, continuously or in a combination of one of the three variants. The processes are endothermic or exothermic and can be conducted isothermally or adiabatically. According to the chemical product, the process can be conducted in the gas phase or liquid phase, with or without solvent, or in the melt. The workup and purification of the chemical product thus obtained can be effected by one of the standard methods in the art, for example crystallization, washing or distillation, or in a combination of these workup methods.

Chemical intermediates and end products are, for example, (poly)isocyanates and precursors thereof, polycarbonates and precursors thereof, active pharmaceutical ingredients and precursors thereof, or active ingredients for crop protection and precursors thereof.

The quality of a process for preparing chemical products is firstly defined by the content of unwanted by-products in the product of the process. Secondly, the quality of a process is defined in that the whole operation of startup and normal production until the operation is run down can be executed without technical production outage or problems that necessitate intervention in the operation, and that there are no losses of feedstocks, intermediates or end product.

Ideally, therefore, the industrial scale plants for performance of such preparation processes are designed such that the processes run in a robust manner in the event of appropriate quality of the auxiliaries and feedstocks used and correct choice of process parameters such as pressure, temperature, ratios of amount and concentrations of the auxiliaries and feedstocks, etc. This means that, in such continuously operated large-scale plants, there will ideally be no problems such as the formation of precipitates, which can settle out in plant equipment or block pipelines.

The startup and shutdown of continuously operated large-scale chemical plants poses particular challenges for the person skilled in the art, caused by the problems that can occur spontaneously therein. Such problems include, for example, cessation of the reaction, elevated energy demand to start the reaction, incomplete reaction which can lead to overloading of the workup, formation of elevated amounts of unwanted by-products which can lead to quality and/or safety problems, deactivation, damage to or carbonization of catalysts, formation of deposits which can block the equipment, or caking of product, by-products and/or substrates.

Production shutdowns that necessitate the shutdown and startup of the plant are an everyday occurrence in industry. Such a shutdown may be an inspection shutdown which is planned in advance, for which purpose the plant is run down, the energy sources are switched off and typically all plant sections that are to be inspected are opened and cleaned for the purpose of examination. Such an inspection may take one or more weeks. After the inspection has ended, the production plant is closed, optionally inertized and provided with auxiliaries and, once the appropriate energy sources and raw materials are available, the production plant can be started up again. However, a production shutdown is not necessarily associated with opening or another mechanical intervention into a reactor or another apparatus in the plant, but may also be connected to the shutdown and restart of the production plant for various other reasons, for example in the event of outage of the raw material supply. In such a case, the plant is typically run in part-load operation and, in the worst case, when the logistical supply chain is interrupted, has to be shut down. Furthermore, production shutdowns may be forced by requirements for maintenance, cleaning or repair in the production plant. In the nitrobenzene process, for example, shutdowns are described as short when production is interrupted for up to one day. It is a feature of all these production shutdowns in practice that there are losses of production, and that, on restarting of the plant, for example when inertization is necessary, nitrogen is consumed or, in the heating of the plant or the feedstocks, energy has to be supplied in the form of steam and power.

The person skilled in the art is aware that an industrial process operated semicontinuously or continuously proceeding from a production plant in operation cannot be switched instantaneously to a production shutdown, but has to be run down in a controlled manner beforehand. This is also the case for a plant stoppage in the event of an emergency. In order to be able to produce again after a production shutdown, the plant has to be run back up to the process parameters before the production shutdown. Reactants and apparatuses have to be heated up, apparatuses may have to be inertized, and the loading of the apparatuses with the reactants is gradually increased to the desired target value. During this startup phase, there is still loss of production, and a disproportionate amount of energy has to be expended in order to prepare the cooled plant for startup and then to run it up to the desired target value with observation of all operationally relevant parameters as well.

A further disadvantage is that, in the event that maintenance, repair and cleaning operations are necessary on or in a reactor or another plant section, it is regularly necessary always to switch off all plant sections since the process steps build on one another and hence always proceed successively. As a result, it is necessary to empty the entire plant, which leads to a considerable amount of reject material. Furthermore, energy has to be expended in order to bring reactors and plant sections back to the respective operating temperatures. Such production shutdowns for plant inspections, repair, maintenance and cleaning measures or shortfalls of raw material or auxiliary that occur, whether planned or unplanned, are therefore recurrent plant states which have a considerable influence on the economic operation of a plant or process that works continuously.

The current prior art processes for industrial scale preparation of chemical products do generally succeed in preparing the desired products with high yield without significant loss of quality in the respective end products, but the literature describes almost exclusively processes in normal operation.

Only for a few industrial scale processes are there descriptions relating to avoidance of problems during the startup and shutdown phase of these processes. For instance, WO 2014/016292 A1 describes the startup of the process for nitrobenzene preparation, wherein the starting material used is a benzene containing less than 1.5% aliphatics, one effect of which is that an improved reaction rate of the reaction is ensured, which saves steam and minimizes the formation of the picric acid by-product. Similar positive effects are described by WO 2014/016290 A1 in relation to the startup procedure for the nitration of benzene to nitrobenzene, wherein circulating sulfuric acid containing less than 1.0% nitrobenzene is used, one effect of which is to save steam, since the workup is not burdened by additional benzene that occurs through incomplete nitration, and the formation of the dinitrobenzene and picric acid by-products is minimized.

The industrial scale continuous preparation of aniline by hydrogenation of nitrobenzene is described in WO 2013/156410 A1, wherein specific reference is made to the startup of the hydrogenation process after regeneration of the hydrogenation catalyst. This involves undertaking an exchange of water in a liquid ring compressor, in order to separately dispose of carbon dioxide present therein, which avoids blockages and corrosion in the waste air system by ammonium carbonate. WO 2013/156409 A1 likewise describes the preparation of aniline, with attention given to the shutdown of the hydrogenation of nitrobenzene, the inventive procedure in the shutdown of the reaction involving the presence of hydrogen for long enough in a sufficient amount in the reaction spaces for all nitroaromatics to have reacted with hydrogen and hence complete depletion thereof during the shutdown operation of the hydrogenation. This prevents increased by-product formation and carbonization of the catalyst by nitrobenzene residues which are hydrogenated with too small an excess of hydrogen. Furthermore, the cost and inconvenience associated with catalyst regeneration is minimized and the service life of the reactors is prolonged.

Patent application WO 2006/125759 A1 is concerned with a Fischer-Tropsch production plant and a process for preparing hydrocarbons. Matters that the patent application addresses are how production operation can still be maintained at least to a restricted degree for a limited time in the event of disrupted availability of methane, and how the production plant can be run down in a controlled manner. One way in which this is achieved is by provision of a reservoir tank 20 for liquefied natural gas. It is mentioned that it can be advantageous, for example, in the event of emergency switch-off of the gasifying unit, to keep the unit at relatively high temperature in order to be able to accomplish the later startup more quickly (called "hot standby"). Also described is an embodiment in which a distillation unit 18 is connected downstream of a hydrocracking reactor 16 and a partial stream of the output from the distillation unit 18 can be recycled into the hydrocracking reactor, while the remaining output from the distillation unit 18 is sent to its normal end use (cf. FIG. 1). No general teaching relating to circulation operation of individual plant sections during the simultaneous complete shutdown of other plant sections in such a way that maintenance operations, for example, can be conducted in these other plant sections can be inferred from this patent application.

Patent application US 2008/026112 A1 is likewise concerned with Fischer-Tropsch processes, specifically with the case of temporary interruption of production in a triphasic reaction zone comprising a liquid phase, a gas phase and a phase comprising suspended catalyst particles. What is disclosed is interruption of the reactant supply and inertization of the reaction zone with an inhibiting gas. An embodiment is described in which the inhibiting gas is recycled into the lower portion of the reaction zone in order to keep the catalyst particles in suspension. In general, the reaction is followed by a condensation step and a separation step, in which case the gas phase from the separation step is recycled into the lower portion of the reactor. To restart the reaction, the reaction zone is charged with an activating gas. No general teaching relating to circulation operation of individual plant sections during the simultaneous complete shutdown of other plant sections in such a way that maintenance operations, for example, can be conducted in these other plant sections can be inferred from this patent application.

Patent application WO 2013/053371 A1 is concerned with a method of providing a methane-rich product gas and an arrangement suitable for the purpose. In the event of a lack of hydrogen, the reactor is operated on standby (without further continuous reactant gas supply). At the changeover between normal operation of the reactor and the standby state, there is intermittent formation of a product gas that does not meet the usual quality demands (also referred to as "inferior gas"). This inferior gas, after restarting of normal operation, is at least partly recycled to a process step that precedes the methanization. This is preferably accomplished by gradually feeding in intermediately stored inferior gas with a time delay. With regard to the standby operation itself, the patent application gives barely any information. It is disclosed merely that the reactor can be purged, for example with hydrogen gas. No general teaching relating to circulation operation of individual plant sections during the simultaneous complete shutdown of other plant sections in such a way that maintenance operations, for example, can be conducted in these other plant sections can be inferred from this patent application.

Patent application US 2005/0227129 A1 is concerned with a heating apparatus for fuel cell power plants. The fuel cell power plant comprises—cf. FIG. 1 and the accompanying text passages—three reactors, namely a reformer (3), a carbon monoxide converter (4) for reaction of carbon monoxide with steam, and a further converter (5) for reaction of carbon monoxide with oxygen. Chemical reactions take place in all these reactors. Without retrofitting measures, they are unsuitable for working up and purifying the process product of a chemical reaction with removal of secondary streams. The heating apparatus according to US 2005/0227129 A1 comprises a burner (6) and conduits (71 to 73) for the supply of hot combustion gases for the purpose of heating the fuel cell power plant. Controlled recycling of the starting stream from an apparatus through these conduits as input stream into this or an upstream apparatus is obviously not envisaged, and does not appear possible either without further retrofitting measures such as the incorporation of additional valves. Thus, no general teaching relating to circulation operation of individual plant sections during the simultaneous complete shutdown of other plant sections in such a way that maintenance operations, for example, can be conducted in these other plant sections can be inferred from this patent application either.

What would be desirable would thus be processes and plants for preparation of chemical products where it is possible to optimize production shutdowns in the course of operation of the respective operations in terms of time taken and possibly also with regard to energy and material consumption. These would lead to a not inconsiderable improvement in the productivity and hence the economic viability of industrial scale chemical production operations and the corresponding plants.

SUMMARY OF THE INVENTION

It has been found that, surprisingly, this object is achieved when (expressed in simplified form and without restriction thereto), during a brief shutdown, so many plant sections as possible are put in circulation mode ("on standby"), in order to be able to start up the overall plant again immediately after the measure. It has also been found that, surprisingly, the energy consumption in the plant put in circulation mode, under some circumstances, is lower than in the case of complete switch-off and restart of the overall plant. By means of a controlled circulation mode in the plant sections that are not affected by the brief shutdown, various advantages are implemented, as is still to be elucidated in detail further down.

The present invention therefore provides the following:

A process for preparing a chemical product or a chemical composition, comprising the steps of:
(I) reacting at least one substrate in a reactor to form at least one chemical product or a chemical composition, the at least one substrate being introduced into the reactor with a mass flow $m_1$;
(II) working up the reaction mixture obtained in step (I) in a workup apparatus to obtain a crude product and at least one secondary stream comprising the constituents separated from the crude product; and the optional steps (III) to (V) of
(III) purifying the crude product obtained in step (II) in at least one purifying apparatus to obtain a purified end product and at least one secondary stream comprising the constituents separated from the purified end product;
(IV) working up the at least one secondary stream obtained in step (II) in a workup unit;
(V) working up the at least one secondary stream obtained in step (III) in a workup unit,
wherein
in the event of shutdown of one or more plant sections from steps (I) to (V), if they are conducted, the mass flow $m_1$ in step (I) is reduced to zero and, in at least one of the plant sections that has not been shut down, the output stream of the plant section is used again as input stream for the respective plant section or an upstream plant section. This process of the invention preferably comprises steps (I) to (III), more preferably steps (I) to (IV), and most preferably steps (I) to (V).

The present invention further provides a plant for preparation of a chemical product or a chemical composition, as is still to be described in detail further down, and which is suitable for the performance of the process of the invention.

Finally, the present invention provides a method of operating a plant for preparation of a chemical product or a chemical composition, which is still to be described in detail further down.

DETAILED DESCRIPTION

Figure 1:
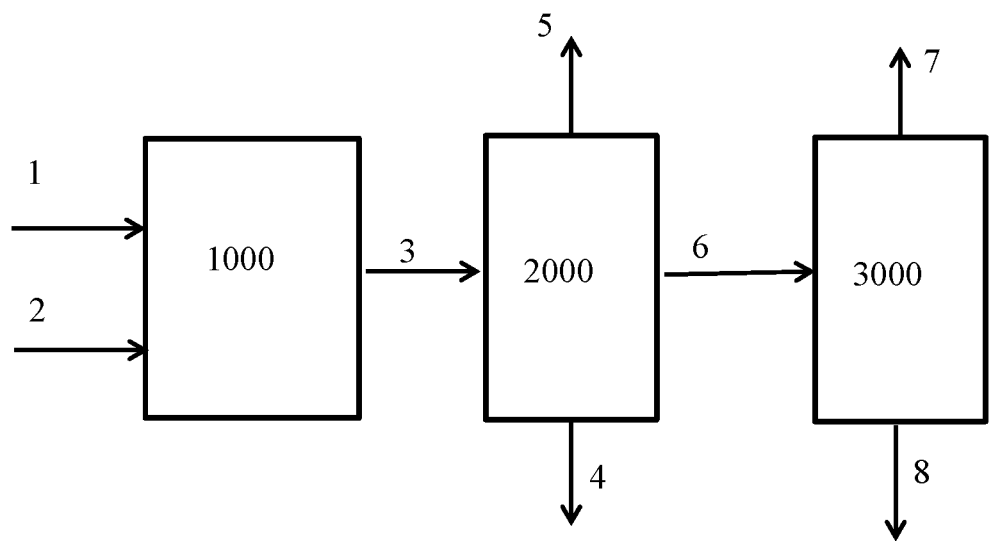
FIG. 1 illustrates the overall concept of a production plant for a chemical product or a chemical composition in regular operation in which two substrates (1) and (2) are supplied to a reactor (1000), the resultant mixture (3) is separated in a workup apparatus (2000) into an aqueous phase (4) and a gaseous phase (5) which contains gaseous secondary components, and a product-containing organic phase (6), which can be purified in the purifying apparatus (3000) to yield the desired product (8) with the separation of secondary components (7).

The term at least one "substrate" refers to any chemical starting material. For example, it is conceivable to convert a substrate 1 (i.e. just one) without further reactants through the action of elevated temperature and/or elevated pressure to the desired product. In another preferred embodiment, two or more substrates can also be reacted with one another in the reactor from step (I). In one embodiment of the present invention, for example, at least two substrates can be reacted in the reactor from step (I), in which case the second substrate 2 is introduced into the reactor from step (I) with a mass flow $m_2$. Preferably, in that case, in the event of shutdown of a plant section, both mass flows, $m_1$ and $m_2$, are reduced to zero. If n substrates i react in step (I), where n is a natural number from preferably 1 to 5, more preferably 1 to 4, most preferably 1 to 3, on shutdown of a plant section, preferably all n mass flows $m_i$ are reduced to zero.

A "shutdown" of a plant section is understood to mean the stoppage thereof, such that an inspection, repair, maintenance or cleaning measure can be conducted in the plant section. The present invention makes it possible to implement an inspection, repair, maintenance or cleaning measure in a plant section without having to shut down the entire production plant. Instead, the present invention enables operation of plant sections not affected by the inspection, repair, maintenance or cleaning measure, or of the corresponding process steps, in a "circulation mode". Since, on shutdown of a plant section, in accordance with the invention, the mass flow rate $m_1$ is reduced to zero, production is stopped during this period. This is especially understood to mean a comparatively short production shutdown (preferably with a duration of 1 hour to 5 days, more preferably of 1 hour to 3 days and most preferably of 1 hour to 2 days) for inspection, repair, cleaning or maintenance purposes in parts of the plant or, for example, to tide the plant over during a shortage of feedstocks or auxiliaries for a limited period of time. The present invention does not concern the case of having to shut down a production plant entirely (i.e. all plant sections), for instance for a plant inspection. According to the invention, the term "shutdown" accordingly encompasses, in the case of presence of m plant sections within the meaning of the present invention (in this regard, see also the paragraph which follows), where m is a natural number, the shutdown of a maximum of m−1 of these plant sections. According to the invention, at least one plant section is thus not "shut down" (i.e. "completely stopped"). Preferably, the present invention is concerned with the case of shutdown of 1 to 2 plant sections, more preferably of 1 plant section. According to the invention, therefore, in the case of shutdown of a plant section (or two or more plant sections, but not all plant sections), the formation of further product is always interrupted (since the mass flow rate of the at least one substrate $m_1$ is being reduced to zero and, therefore, no further product can be produced). Also encompassed by the invention, however, is the case that the reactor from step (I) is being operated in circulation mode (in this regard, see also the paragraph which follows) and another plant section within the meaning of the above definition is being shut down (cf., for example, FIG. 3).

"Circulation mode" is understood in the context of this invention to mean that the output stream of a plant section is used as input stream for this plant section or an upstream plant section (i.e. upstream in terms of flow). In this context, "plant section" means the plant section corresponding to the respective step (I) to (V), if they are conducted, in a plant for preparation of chemical products by the process of the invention. For example, the plant section of step (I) comprises "a reactor", this term also encompassing embodiments in which two or more reactors (for example a cascade of two or more reactors connected in series) are used (in other words, the word "a" in this connection and in connection with other apparatuses of other plant sections as well should be regarded as the indeterminate article and not to mean the number "one"). Reactors connected in parallel or in series are known in the prior art in the preparation of chemical products as well, and can also bring advantages in particular dimensions and operational characteristics. The plant of the invention and the process of the invention therefore also provide for preferred embodiments in which reactors connected in series or in parallel are employed with preference, especially in step (I).

A plant section from one of steps (I) to (V) may thus comprise a plurality of apparatuses, including different apparatuses.

The plant section from step (II) comprises a workup apparatus, i.e. a phase separation apparatus for separation of a polyphasic crude product into, for example, an aqueous phase comprising water of reaction, an organic phase comprising the desired product, and a gas phase comprising gaseous by-products and/or co-products and optionally added inert gases.

Such secondary streams as an aqueous stream composed of water of reaction and a gaseous stream composed of by-products and/or co-products and optionally added inert gases are preferably subjected to further workup in step (IV). The plant section from step (IV) comprises a workup unit for this purpose. This workup unit may comprise different individual apparatuses, for example a device for distillation or stripping of the at least one secondary stream from step (II). Step (IV) can also occur more than once. One example is the case that the workup of secondary streams from step (II) is distributed between two or more plant sections. This may especially be the case when one plant section is provided for the workup of a liquid secondary stream, and one plant section for the workup of a gaseous secondary stream. In this case mentioned by way of example, the process comprises two steps (and plant sections) of the category (IV) which are conducted in parallel alongside one another, namely the workup of the liquid secondary stream in a workup unit (step (IVa)) and the workup of the gaseous secondary stream in a further workup unit (step (IVb)).

The plant section from step (III) comprises a purifying apparatus, for example a distillation apparatus.

The at least one secondary stream removed in the purification in step (III) is preferably subjected to further workup in step (V). The plant section from step (V) comprises a workup unit for this purpose. This workup unit may comprise different individual apparatuses, for example a device for distillation or stripping of the at least one secondary stream from step (III). Step (V) can also occur more than once. One example is the case that the workup of secondary streams from step (III) is distributed between two or more plant sections. This may especially be the case when one plant section is provided for the workup of a liquid secondary stream, and one plant section for the workup of a gaseous secondary stream. In this case mentioned by way of example, the process comprises two steps (and plant sections) of the category (V) which are conducted in parallel alongside one another, namely the workup of the liquid secondary stream in a further workup unit (step (Va)) and the workup of the gaseous secondary stream in a further workup unit (step (Vb)).

It will be appreciated that the plant sections, as well as the apparatuses detailed explicitly above, may also include peripheral equipment, for example pumps, heat exchangers and the like.

The circulation mode can be established over several apparatuses of a plant section. For example, the output stream from the last apparatus of a plurality of apparatuses connected in series in a plant section may be used as input stream for the first apparatus of the apparatuses connected in series in this plant section. It is also possible to apply the circulation mode only to a portion of the apparatuses of a plant section, for example when the output stream of the last apparatus of a plurality of apparatuses connected in series in a plant section is recycled not into the first but into a further apparatus of this plant section.

The circulation mode can also be established over two or more plant sections. For example, the output stream of the last apparatus of a plant section, for example of a plant section from the purification step (III), can be used as input stream for the first apparatus of an upstream plant section, for example of a plant section from the workup step (II), in which case the circulation mode is established in that the output stream of the workup step (II) mentioned by way of example serves as input stream for the purification step (III).

Steps (I), (II) and (III) of the process of the invention are preferably conducted within a continuous operation. Preferably, steps (IV) and (V) are also conducted within a continuous operation.

The stopping of $m_1$ (and if appropriate of $m_2$; in the case of n substrates i preferably the stopping of all n mass flows $m_i$), i.e. the mass flow of the at least one substrate(s) into the reactor from step (I), ensures that, during the interruption which, as described above, is implemented for the purpose of inspection, maintenance, repair and/or cleaning of a section of the production plant or was caused by a shortage of raw material(s) and/or auxiliary/auxiliaries, the reaction in step (I) does not continue to take place. This, and the use of the output stream of at least one uninterrupted step and corresponding plant section as input stream for the respective step and corresponding plant section (or for an upstream step or plant section), ensures that these steps and corresponding plant sections are each run "in a circuit".

For this purpose, it is preferable that the process of the invention comprises step (III). In this way, the effects of the invention are manifested to a particular degree. In a particularly preferred embodiment, the process of the invention also comprises steps (IV) and (V).

In a further preferred embodiment of the present invention, in the event of shutdown of a plant section from at least one of steps (I) to (V), if they are conducted, the output stream in every plant section that has not been shut down is used again as input stream for this or an upstream plant section.

The advantages of the process of the invention also arise for multistage processes in which reactions that build on one another in successive plant sections are conducted, in order thus to arrive at a reaction product built up in this way. Thus, the process of the invention, in a further preferred embodiment, comprises a further step (Ia) in which at least one third substrate is reacted with the product of the reaction from step (I) in the same or a further reactor, and the at least one third substrate is introduced into the reactor from step (Ia) with a mass flow $m_3$. In the context of the present invention, other possible processes are those in which a multitude of reactions are conducted in successive reactors, for example three, four, five, six or more. Thus, cascade reactions, tandem reactions or domino reaction regimes in one reactor or in successive reactors are also possible in the context of the present invention and, by virtue of the efficiency in the formation of chemical compounds, are also advantageous and therefore preferred.

It is especially preferable that, when the supply of the at least one substrate, or optionally of all substrates, is stopped, the supply of solvent, if the reaction is one in the liquid phase, is not interrupted. This can advantageously achieve the effect that, firstly, any formation of by-products can be prevented and, secondly, no lumps are formed in the reaction mixture. It is thus possible to efficiently purify the desired product, and prevent blockage of plant equipment, for example of pipelines, valves and pumps, and the production of off-spec material.

In addition, it is especially preferable that, when the supply of the at least one substrate, or optionally of all substrates, is stopped, the supply of inert gas, if the reaction is one in the gas phase, is not interrupted. This can advantageously achieve the effect that, firstly, any formation of by-products can be prevented and, secondly, for example, blockage of plant equipment, for example of pipelines, valves and pumps, and the production of off-spec material are prevented.

The chemical product of the process of the invention may preferably be a polycarbonate or one of its precursors, an isocyanate or one of its precursors, an active pharmaceutical ingredient, an olefin, aromatic, polyolefin or the like.

Examples of di- and polyisocyanates here include aromatic di- and polyisocyanates, for example methylene diphenyl diisocyanate (mMDI) as isomers or as isomer mixture, polymethylene polyphenyl polyisocyanate (pMDI), mixtures of methylene diphenyl diisocyanate and polymethylene polyphenyl polyisocyanate (MDI), tolylene diisocyanate (TDI) as pure isomers or isomer mixture, isomers of xylylene diisocyanate (XDI), isomers of diisocyanatobenzene, xylene 2,6-isocyanate, naphthylene 1,5-diisocyanate (1,5-NDI), diisocyanates based on aliphatic or cycloaliphatic hydrocarbons having 2 to 18 carbon atoms, for example butane 1,4-diisocyanate, pentane 1,5-diisocyanate, hexane 1,6-diisocyanate (HDI), octane 1,8-diisocyanate, nonane 1,9-diisocyanate, decane 1,10-diisocyanate, 2,2-dimethylpentane 1,5-diisocyanate, 2-methylpentane 1,5-diisocyanate (MPDI), 2,4,4 (or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4 (3)-isocyanatomethylcyclohexane (AMCI), 1,3 (and/or 1,4)-bis (isocyanatomethyl)cyclohexane, bis(isocyanatomethyl) norbornane (NBDI), 4,4'(and/or 2,4')-diisocyanatodicyclohexylmethane, and (cyclo)aliphatic triisocyanates having up to 22 carbon atoms, for example triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane or 1,3,5-tris(isocyanatomethyl)cyclohexane.

The amines corresponding to the above polyisocyanates are aromatic di- and polyamines, for example methylenediphenyldiamine (mMDA) as isomers or as isomer mixture, polymethylenepolyphenylpolyamine (pMDA), mixtures of methylenediphenyldiamine and polymethylenepolyphenylpolyamine (MDA), tolylenediamine (TDA) as pure isomers or isomer mixture, isomers of xylylenediamine (XDA), isomers of diaminobenzene, 2,6-xylidine, naphthylene-1,5-diamine (1,5-NDA), diamines based on aliphatic or cycloaliphatic hydrocarbons having 2 to 18 carbon atoms, for example 1,4-diaminobutane, 1,5-diaminopentane, 1,6-diaminohexane (HDA), 1,8-diaminooctane, 1,9-diaminononane, 1,10-diaminodecane, 2,2-dimethyl-1,5-diaminopentane, 2-methyl-L5-pentanediamine (MPDA), 2,4,4 (or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4(3)-aminomethylcyclohexane (AMCA), 1,3 (and/or 1,4)-bis (aminomethyl)cyclohexane, bis(aminomethyl)norbornane (NBDA), 4,4'(and/or 2,4')-diaminodicyclohexylmethane, (cyclo)aliphatic triamines having up to 22 carbon atoms, for example triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl)heptane, 1,6-diamino-3-(aminomethyl) hexane or 1,3,5-tris(aminomethyl)cyclohexane.

The industrial scale preparation of the polyisocyanates listed above by reacting the corresponding amines with phosgene has long been known from the prior art, the reaction being conducted in the gas or liquid phase and batchwise or continuously (W. Siefken, Liebigs Ann. 562, 75-106 (1949)). Processes for preparing organic isocyanates from primary amines and phosgene have already been described many times before; see, for example, G. Wegener et al. Applied Catalysis A: General 221 (2001), p. 303-335, Elsevier Science B.V. and Ullmanns Encyklopädie der technischen Chemie [Ullmann's Encyclopedia of Industrial Chemistry], 4th ed. (1977), volume 13, p. 351 to 353.

In terms of production volumes, MDI and TDI are the most important polyisocyanate products worldwide.

Modern industrial scale preparation of MDI is continuous, and the reaction is conducted as an adiabatic phosgenation as described in EP 1 616 857 B2 and EP 1 873 142 B1. The workup of the crude MDI is described by way of example in U.S. Pat. No. 5,136,087 (B), EP 1 854 783 A2, EP 1 475 367 B1 or else in EP 1 686 112 A1.

The continuous production of TDI in industry is effected in the gas phase, as described, for example, in EP-A-2 196 455, EP-A-0 289 840, EP-A-0 570 799, EP-B-1 935 875 and EP-B-1 935 876, or in the liquid phase, as described, for example, in EP 0 322 647 B1, WO 2013/139703 A1, EP 314 985 B1, EP 1 371 636 B1, EP 1 371 635 B1 and EP 1 413 571 B1.

The precursor of MDI is MDA. MDA in turn is prepared by condensation of aniline and formaldehyde. Aniline is obtained by hydrogenation of nitrobenzene. Nitrobenzene in turn arises through nitration of benzene, which constitutes the petrochemical basis for preparation of MDI via the individual intermediates.

The continuous or batchwise preparation of MDA is disclosed, for example, in EP 1 616 890 A1, U.S. Pat. No. 5,286,760, EP-A-451442 and WO-A-99/40059.

The continuous preparation of aniline in isothermal or adiabatic mode is effected on the industrial scale generally by catalytic hydrogenation of nitrobenzene, as described, for example, in GB 1 452 466 A1, EP 0 011 090 A1 or EP 0 944 578 A2 (isothermal mode) and in EP 0 696 574 B1, EP 0 696 573 B1, EP 1 882 681 A1 (adiabatic mode). As well as the processes mentioned with stationary catalyst beds, those having fluidized catalyst beds have also been described, for example in DE 1114820 B, DE 1133394 B or WO 2008/034770 A1.

The processes for industrial scale preparation of nitrobenzene that are standard nowadays correspond essentially to the concept of adiabatic nitration of benzene by a mixture of sulfuric acid and nitric acid, which is generally referred to as mixed acid. Such a process was claimed for the first time in U.S. Pat. No. 2,256,999 and is described in current embodiments, for example, in EP 0 436 443 B1, EP 0 771 783 B1 and U.S. Pat. No. 6,562,247 B2. Isothermal processes for nitration of benzene with mixed acid are also known, as described, for example, in EP 0 156 199 B1.

The precursor of TDI is TDA. TDA in turn is obtained by hydrogenation of dinitrotoluene (DNT). DNT in turn arises through nitration of toluene, which constitutes the petrochemical basis for preparation of TDI via the individual intermediates.

The modern continuous preparation of TDA in isothermal and/or adiabatic mode is effected on the industrial scale generally by catalytic hydrogenation of DNT, as described, for example, in detail in WO 2011/086050 A1 and references cited therein.

The preparation of dinitrotoluene by nitration of toluene with nitrating acid (mixture of nitric acid and sulfuric acid) has already been the subject of numerous publications and patent applications (Ullmanns Enzyklopedie der technischen Chemie, 4th edition, volume 17, page 391 ff, 1979, Verlag Chemie Weinheim/New York). The industrial scale preparation is effected by predominantly isothermal means with nitric acid in the presence of sulfuric acid as catalyst in continuous mode, as described, for example, in H. Hermann, J. Gebauer, P. Konieczny, "Industrial Nitration of Toluene to Dinitrotoluene" in ACS-Symposium, Series 623, 234-249, 1996, ed. L. F. Albright, R. V. O Carr, R. J. Schmitt.

Examples cited here of the polycarbonates are polycarbonate and precursors thereof, for example bisphenol A, bisphenol F and other precursors containing hydroxyl groups.

The present invention further provides a plant for preparation of a chemical product or a chemical composition, comprising the plant sections of:

(I) a reactor for execution of the conversion of at least one substrate, preferably of a plurality of (especially two) substrates, (II) a workup apparatus for obtaining a crude product from the product mixture obtained in the reactor (I) alongside at least one secondary stream comprising the constituents separated from the crude product, and optionally and preferably the plant sections (III) to (V), (III) a purifying apparatus for purifying the crude product obtained in the workup apparatus (II) to give a purified end product with removal of at least one secondary stream comprising the constituents separated from the purified end product, (IV) a workup unit for workup of the at least one secondary stream obtained in the workup apparatus (II), (V) a workup unit for workup of the at least one secondary stream obtained in the purifying apparatus (III), wherein the plant is configured such that, in the event of shutdown of one or more plant sections (I) to (V), if they are present, no further introduction of the at least one substrate into the reactor (I) takes place and, independently of one another or simultaneously, in at least one plant section unaffected by the shutdown, the output stream can be recycled and used as input stream for the respective plant section or an upstream plant section. The configuration of the plant in such a way that "in the event of shutdown of one or more plant sections (I) to (V), if they are present, no further introduction of the at least one substrate into the reactor (I) takes place" should be understood to mean that, prior to or simultaneously with the shutdown of a plant section, the substrate supply is interrupted; in other words, prior to or simultaneously with the establishment of circulation mode in at least one plant section unaffected by the shutdown, the substrate supply is interrupted. In terms of apparatus, this can be achieved in various ways, for example by the incorporation of process control units which automatically interrupt the substrate supply on shutdown of one or more plant sections (on adjustment of one or more plant sections to circulation mode). The setting-up of a barrier circuit which enables the adjustment to circulation mode only in the event of an interrupted substrate supply is likewise conceivable. Suitable software and hardware products are commercially available and known to those skilled in the art. Any necessary programming and adaptation operations are within the routine duty which is customary to the person skilled in the art. It will be apparent that this plant is especially configured to be able to conduct the process of the invention. The plant sections mentioned thus correspond to the steps of the process of the invention. Thus, the advantages and effects of the process of the invention also apply to the plant of the invention.

In a preferred embodiment of the plant of the invention, independently of one another or simultaneously, the output stream in every other plant section unaffected by the interruption can be recycled and used again as input stream for the respective plant section or an upstream plant section.

In a preferred configuration, independently of one another, the mass output stream in every other plant section or reactor unaffected by the interruption can be recycled and used again as mass input stream for the respective plant section or reactor. In an alternative configuration, simultaneously, the output stream in every other plant section unaffected by the interruption can be recycled and used again as input stream for the respective plant section or an upstream plant section.

Preferably, the plant of the invention comprises the plant section for purification (III) of the chemical product or the product composition. More preferably, the plant of the invention comprises the workup units (IV) and (V) for workup of secondary streams obtained from plant sections (II) and (III) respectively.

The stopping of $m_1$ (and if appropriate of $m_2$; in the case of n substrates i preferably the stopping of all n mass flows $m_i$), i.e. the mass flow of at least one substrate (if appropriate the mass flows of all substrates) into the reactor (I), ensures that, during the interruption (the shutdown of one or more plant sections) which, as described above, is implemented for the purpose of inspection, repair, maintenance and/or cleaning of a section of the production plant or was caused by a shortage of raw material(s) and/or auxiliary/auxiliaries, the reaction in step (I) does not continue to take place.

It is especially preferable here that, when the supply of the at least one substrate, or optionally of all substrates, is stopped, the supply of solvent, if the reaction is one in the liquid phase, is not interrupted. This can advantageously achieve the effect that, firstly, any formation of by-products can be prevented and, secondly, for example, no lumps are formed in the reaction mixture. It is thus possible to efficiently purify the desired product, and prevent blockage of plant equipment, for example of pipelines, valves and pumps, and the production of off-spec material.

In addition, it is especially preferable that, when the supply of the at least one substrate, or optionally of all substrates, is stopped, the supply of inert gas, if the reaction is one in the gas phase, is not interrupted. This can advantageously achieve the effect that, firstly, any formation of by-products can be prevented and, secondly, for example, blockage of plant equipment, for example of pipelines, valves and pumps, and the production of off-spec material are prevented.

Should two or more production lines or reactor lines be operated in parallel, it is firstly possible in accordance with the invention to put one or more plant sections in one production line or reactor line out of operation and operate the other production line(s) or reactor line(s) in accordance with the invention, if required, successively with regard to the shutdown of one or more accompanying plant sections. Alternatively, it is also possible in the context of the present invention to operate all production lines or reactor lines, if required, simultaneously or near-simultaneously in accordance with the process of the invention with regard to the shutdown of one or more accompanying plant sections of the plant of the invention.

The present invention further provides a method of operating a plant for preparing a chemical product or a product composition during a shutdown of the preparation process, the plant comprising the plant sections of:

(I) a reactor for execution of the conversion of at least one substrate, preferably of a plurality of (especially two) substrates,
(II) a workup apparatus for obtaining a crude product from the product mixture obtained in the reactor (I) alongside at least one secondary stream comprising the constituents separated from the crude product, and optionally and preferably the plant sections (III) to (V),
(III) a purifying apparatus for purifying the crude product obtained in the workup apparatus (II) to give a purified end product with removal of at least one secondary stream comprising the constituents separated from the purified end product,
(IV) a workup unit for workup of the at least one secondary stream obtained in the workup apparatus (II),
(V) a workup unit for workup of the at least one secondary stream obtained in the purifying apparatus (III), the method comprising the steps of:
(i) stopping the supply of the at least one substrate, preferably all substrates, into the reactor (I),
(ii) running at least one plant section in such a way that the output stream of the respective plant section is used as input stream for this plant section or an upstream plant section;
(iii) shutting down at least one plant section.

Step (ii) comprises the measures that are taken in the process of the first subject of the present invention. Thus, reference is made to the above measures of the circulation mode of the invention; these are therefore not repeated in detail again at this point. The plant to be operated is also preferably a plant according to the present invention. With the present process, it is therefore also possible to achieve the above advantages of the present invention.

In a preferred embodiment, the process comprises the steps of:
(iv) optionally opening the at least one plant section shut down in step (iii);
(v) performing a maintenance, cleaning, inspection and/or repair measure in the plant section shut down in step (iii);
(vi) optionally closing and optionally inertizing the at least one plant section from step (v);
(vii) starting up the at least one plant section from step (vi);
(viii) starting the supply of the at least one substrate to the reactor (I).

In this manner, a process with which a maintenance, inspection, cleaning, overhaul and/or repair measure can be conducted in a highly efficient and time-saving manner and with avoidance of wastes in a plant for preparation of chemical compounds is provided.

In a further preferred embodiment, step (ii) in particular comprises the diversion of the output stream of the respective plant section as mass input stream for the respective plant section or an upstream plant section. As in the first subject of the present invention, it is also possible to run two plant sections together in a circuit. This may mean plant sections either connected in parallel or connected in series.

The appended drawings are intended to illustrate the invention in detail:

FIG. 1 shows a production plant for a chemical product or a chemical composition in regular operation:

Two substrates 1 and 2 are supplied to a reactor 1000. The resultant reaction mixture 3 is separated in a workup apparatus 2000 into, for example, an aqueous phase 4, a gaseous phase 5 with gaseous secondary components, for example, and a product-containing organic phase 6. This can be accomplished, for example, in a simple phase separation apparatus. Stream 6 is purified in the purifying apparatus 3000 to give the desired product 8, with separation of secondary components 7. 3000 may, for example, be a distillation apparatus in which low-boiling secondary components 7 are separated from the product 8.

Figure 2:
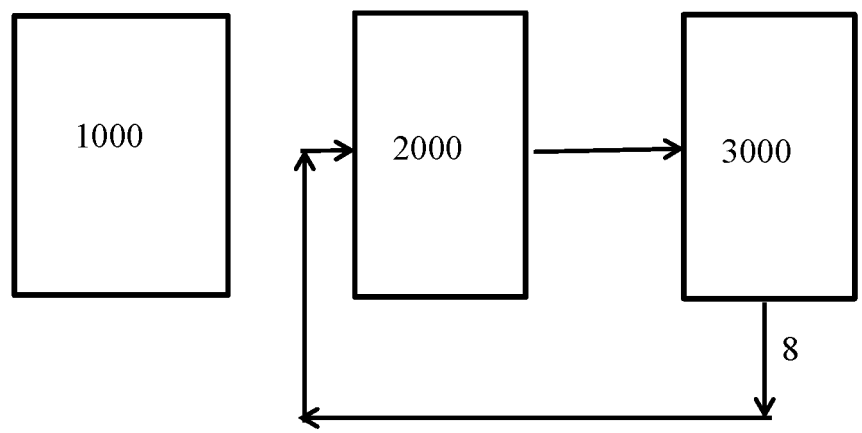
FIG. 2 illustrates a production plant for a chemical product or a chemical composition operating in one possible configuration of a circulation mode of the invention. In this configuration, the reactor (1000) is to put out of operation so the supply of substrates (1) and (2) is interrupted, and the bottoms output (8) from the purifying apparatus (3000) is guided into the phase separation apparatus (2000) and then back into the purifying apparatus (3000).

FIG. 2 shows one possible configuration of a circulation mode of the invention:

The reactor 1000 is to be put out of operation in order, for example, to conduct maintenance operations. For this purpose, the supply of substrates 1 and 2 is interrupted. In the embodiment shown, the bottoms output 8 from the distillation column 3000 is guided into the phase separation apparatus 2000 and thence back into the distillation column 3000.

Figure 3:
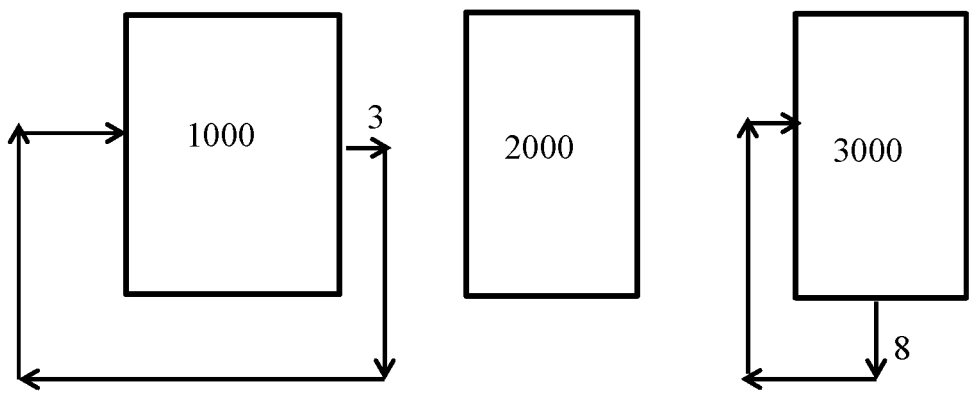
FIG. 3 illustrates a different configuration for operation of a production plant for a chemical product or a chemical composition in circulation mode. In this configuration, the phase separation apparatus (2000) is to be put out of operation, so the supply of substrates (1) and (2) is interrupted and the reaction mixture (3) from the reactor (1000) is guided back into the reactor (1000), while the bottoms output (8) from the purifying apparatus (3000) is recycled back into the purifying apparatus (3000).

FIG. 3 shows a further possible configuration of a circulation mode of the invention:

The phase separation apparatus 2000 is to be put out of operation in order, for example, to conduct maintenance operations. For this purpose, the supply of substrates 1 and 2 is interrupted. In the embodiment shown, the reactor output 3 is recycled into the reactor 1000. At the same time, the bottoms output 8 from the distillation column 3000 is recycled back into the latter.

Figure 4:
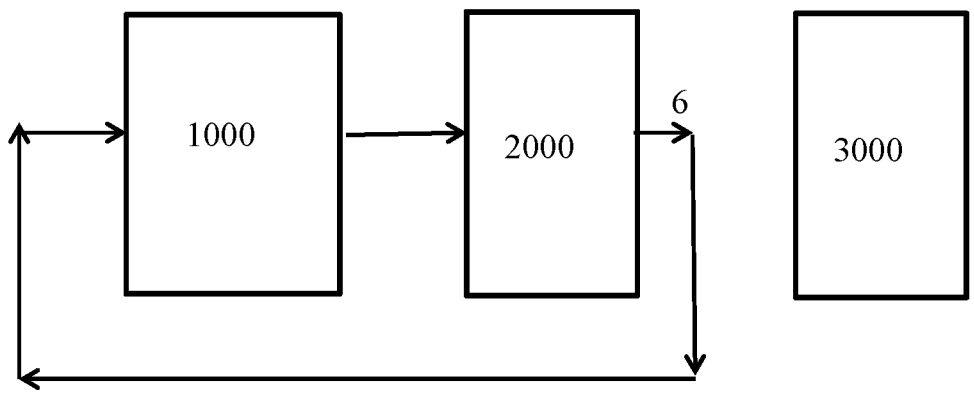
FIG. 4 illustrates another possible configuration of a production plant for a chemical product or a chemical composition in circulation mode. In this configuration, the purifying apparatus (3000) is to be put out of operation, so the supply of substrates (1) and (2) is interrupted and the product-containing organic phase (6) from the phase separation apparatus (2000) is guided back into the reactor (1000) and then into the phase separation apparatus (2000).

FIG. 4 shows a further possible configuration of a circulation mode of the invention:

The distillation column 3000 is to be put out of operation in order, for example, to conduct maintenance operations. For this purpose, the supply of substrates 1 and 2 is interrupted. In the embodiment shown, the output of organics 6 from the phase separation apparatus 2000 is recycled into the reactor 1000 and thence into the phase separation apparatus 2000. Residual amounts of aqueous phase still present in 2000 are either discharged or remain in the apparatus.

The process of the invention gives rise to the following advantages:
i) increase in productivity, because the availability of the plant increases, since the time taken for the running down and restarting of the plant for the production shutdown is greatly minimized.
ii) There are no capital costs for a greater plant capacity.
iii) There are no capital costs for a larger end product tank for buffering of prolonged shutdown times.
iv) Avoidance of excess waste products, wastewater and offgases that have to be purified additionally. These would arise if the plant had to be completely restarted.
v) In many cases, energy savings arise because there is no need for the preparations required for the shut-down plant sections that are needed for the restart, such as the heating of the auxiliaries and feedstocks or the heating of the equipment etc.
vi) In many cases, there are savings of auxiliaries such as condensate and nitrogen.
vii) The susceptibility of pumps or compressors to need repair is reduced, since the slip-ring seals thereof suffer from every restart when they are switched off in the event of a shutdown. Thus, subsequent repairs are avoided, which again has a positive effect on the productivity of the plant and maintenance costs.

These advantages i) to vii) may each occur individually or advantageously in combination.

The success of the procedure of the invention is surprising to the person skilled in the art because, in principle, in order to save energy and to be able to concentrate on the maintenance measures due in the production shutdown, the skilled person would be much more likely to shut down the entire plant, especially since additional capital costs for recycling pipelines including pumps, retrofitting in the apparatuses and additional process control technology have to be accepted for the process of the invention and for the plant of the invention.

The present invention is to be illustrated hereinafter by means of examples.

EXAMPLES

Content figures in ppm or % are parts by mass based on the total mass of the respective material/stream. Analysis values, unless stated otherwise, were determined by means of gas chromatography.

General Conditions for the Preparation of Nitrobenzene in a Run-In Production Plant At a production load of 50 t/h of nitrobenzene, a sulfuric acid stream, a nitric acid stream, a fresh benzene stream and a return benzene stream were metered into a nitration reactor. A 5% to 10% excess of benzene was used, based on nitric acid. On completion of conversion of the nitric acid with the benzene to give nitrobenzene in an adiabatic reaction regime, the reaction product, now at about 130° C., was fed to a phase separation apparatus in which the reaction product separated into an organic phase (=crude nitrobenzene, also containing benzene as well as nitrobenzene) and an aqueous phase (=waste acid, also containing small proportions of nitrobenzene and benzene as well as sulfuric acid). The aqueous phase comprising mainly sulfuric acid was subjected to a flash evaporation of water by abruptly lowering the pressure in the evaporator, and concentrated in this way. The concentrated sulfuric acid was stored in the sulfuric acid tank for reuse. After being removed in the phase separation apparatus, the crude nitrobenzene was cooled down to about 50° C. in the crude nitrobenzene cooling operation and sent to the washing operation. The stream of purified crude nitrobenzene which had been substantially freed of nitrophenols and salts and had been obtained in this way was heated up again and, in a distillation column, freed of water, benzene and other low boilers which were removed overhead, giving dried pure nitrobenzene. The condensed top product from the distillation column was fed to a phase separation apparatus in which the top product separated into an organic phase (comprising benzene) and an aqueous phase. The organic phase was stored intermediately in a buffer tank and thence run back, as already described above, into the feed of the nitration reactor for reaction. The power consumption of such a plant is about 890 kW/h.

Nitrobenzene prepared in this way typically has a purity of about 99.96% (GC), a residual benzene content of 0.0028% (GC), a 1,3-dinitrobenzene content of 0.0273% (GC) and a nitrophenol content of <5 ppm (HPLC). In addition, the nitrobenzene has a water content of 0.0079% (determined according to Karl Fischer).

Comparative Example 1: Brief Shutdown of a Production Plant with Complete Stoppage of the Plant, Cleaning Measure and Restarting of the Plant The brief shutdown of the plant served for conduction of cleaning operations in the nitration region. For this purpose, the plant was run down completely, i.e. nitration, washes, distillation, acid water workup and alkaline wastewater workup. The energy supplies were switched off during the cleaning operations. After the cleaning operations, the plant was started up again, for which it was necessary to inertize, fill and heat the entire plant beforehand.

Procedure for the Complete Stoppage of the Plant:

First, the nitration was shut down: The metering pumps for the input streams of benzene and nitric acid were switched off. The vapor from the flash evaporator was stopped 5 minutes after the benzene and nitric acid raw materials. The circulation of sulfuric acid continued for 1 hour until all organics had been discharged from the nitration circuit consisting of nitrators, phase separation apparatus, flash evaporator and circulating sulfuric acid reservoir tank. Then the circulation of sulfuric acid at 100° C. was interrupted by switching off the circulation pump. The nitrators, the phase separation apparatus and the flash evaporator were left under standing sulfuric acid. The remaining circulating sulfuric acid was in the sulfuric acid reservoir tank. The total inventory of sulfuric acid was 74 tonnes. Simultaneously with the circulation pump, the vacuum pump to the flash evaporator was switched off and the vacuum was broken with nitrogen. The nitration circuit was then at rest. Time taken 2 hours, without breaking the vacuum 1 hour.

Thereafter, the acid water workup was shut down by interrupting the feed of acidic wastewater from the acid water reservoir tank to the acid water stripper. The steam to the acid water stripper and the bottoms pump of the stripper were stopped. The acid water workup was then at rest. The time taken was 5 minutes.

Next, the washes were shut down by interrupting the crude nitrobenzene feed from the crude nitrobenzene tank to the acidic wash. The crude nitrobenzene pathway through the acidic, alkaline and neutral wash was stopped by stopping the delivery pumps for the crude nitrobenzene upstream of the respective washes. The washes had an operating temperature of 48° C. and remained filled with crude nitrobenzene. At the same time, the acidic, alkaline and neutral wash water pathway was stopped by switching off the respective pumps. The time taken was 5 minutes.

Then the distillation was shut down by interrupting the feed of crude nitrobenzene and taking away the steam to the distillation column Immediately thereafter, the product discharge was interrupted by switching off the bottoms pump and the return stream at the top of the column was stopped by stopping the benzene pump. After the vacuum pump had been switched off and vented with nitrogen, the distillation was at rest. The time taken was 5 minutes.

Lastly, the alkaline wastewater workup was shut down by setting the thermal pressure decomposition to circulation mode and stopping the steam to the pressure decomposition. At the same time, the supply and removal of the alkaline wastewater to and from the stripper was stopped by switching off the wastewater pumps and stopping the steam to the stripper. The time taken was 5 minutes. The circulation mode of the thermal pressure decomposition (TDZ) was stopped after 10 hours, as soon as the circulation water had been cooled below 100° C.

The complete stoppage took a total of two hours without purging and emptying of the apparatuses, pumps and pipelines, neglecting the running-down of the TDZ. In modern automated production plants, the number of personnel required for the running-down operation only plays a minor role.

Procedure for the Cleaning Measure:

It was necessary to clear a blockage in the benzene preheater in the feed of the crude nitrobenzene from the phase separation apparatus to the crude nitro tank:

First of all, the level in the phase separation vessel was lowered by 50%, in order that no further organic material could run into the benzene preheater to be cleaned. Subsequently, the benzene preheater was purged with condensate through a purging stub mounted between the phase separation apparatus and benzene preheater for 1 hour, in order to remove crude nitrobenzene and traces of sulfuric acid. The purge condensate was led off to the acidic wash. Thereafter, the benzene preheater was mechanically divided from the inlet and outlet, and black precipitates in the benzene preheater that constituted the blockage were rinsed out with large amounts of condensate using two further purging stubs to the water treatment plant. The time taken was 3 hours. After all 3 purging stubs had been disassembled, the inlet and outlet of the benzene preheater were mounted. The time taken for this was 2 hours. Thereafter, the pipelines affected were heated up and cooled down several times, in the course of which the flange connections were re-tightened with the new seals. The time taken was 2 hours.

The cleaning measure took a total of 8 hours. In modern automated production plants, the number of personnel required for the preparation for the cleaning measure, namely partial emptying of the plant, mounting of the purging stub for preliminary cleaning of the benzene preheater with inlet and outlet and subsequent preliminary cleaning with condensate, plays an important role. In this case, one additional production worker is required. Workmen for the disassembly and assembly of the pipelines for the cleaning measure and the cleaning personnel themselves are likewise required.

Procedure for the Restarting of the Plant:

The vacuum pumps in the entire production plant were put in operation beforehand. The phase separation apparatus and the cleaned benzene preheater were inertized with 100 m$^3$ (STP) of nitrogen.

Firstly, the washes were started by starting the crude nitrobenzene pump to put the crude nitrobenzene supply from the crude nitrobenzene tank to the acidic wash in operation. Thereafter, the acidic, alkaline and neutral wash water pathway was started by switching on the respective pumps. Then the crude nitrobenzene pathway through the acidic, alkaline and neutral wash was started by switching on the delivery pumps for the crude nitrobenzene upstream of the respective washes. The washing apparatuses that were filled with crude nitrobenzene and wash water were at 45° C. and warmed gradually back up to 48° C. after the production plant had been started.

Once the last stage of the neutral wash had been put in operation by feeding in 3° t/h of condensate, the distillation was started by applying vacuum to the distillation column and running crude nitrobenzene at 45° C. from the last neutral wash to the distillation column. Thereafter, the bottoms pump of the column was started and crude nitrobenzene was run to the crude nitrobenzene tank. Then the distillation column was supplied with 2 t/h of 16 bar steam and heated up to 170° C. At 50° C. at the top of the column, the reflux was put in operation by starting the benzene pump. The washes and the distillation were ready for restarting of the production plant after 4.5 hours.

In parallel to the washes and distillation, the acid water workup was started by applying 1 t/h of 6 bar steam to heat up the acid water stripper and starting the bottoms pump of the stripper. Subsequently, the feeding of the acidic wastewater from the acid water reservoir tank to the acid water stripper was started. Then the acid water workup was ready for restarting of the production plant. The time taken to start the acid water stripper including the analysis of the acidic wastewater for organics by means of gas chromatography was 1 hour.

In parallel to the washes and the distillation, the alkaline wastewater workup was started by supplying thermal pressure decomposition which had been put in circulation mode with 0.6 t/h of 110 bar steam, in order to bring the circulation water from 85° C. to 285° C. 2 hours prior to the discharge of the alkaline wastewater, the stripper was supplied with 0.5 t/h of 6 bar steam and the inlet and outlet of the alkaline wastewater to and from the stripper were started by starting the wastewater pumps. The time taken was 8 hours.

One and a half hours before the washes and distillation were ready for restarting of the production plant and after the acid water workup was running in circulation mode, the sulfuric acid circulation pump was started and the sulfuric acid was run in circulation through the nitrator, phase separation apparatus, flash evaporator and sulfuric acid reservoir tank. In the flash evaporator, the vacuum was started and then 2.4 t/h of 6 bar steam were applied, which heated the circulating sulfuric acid to starting temperature. This operation took 1 hour until the circulating sulfuric acid cooled down to 93° C. had been heated up to 100° C.

After 4.5 hours, the washes and the distillation were ready for operation and the production plant was started by starting the benzene and nitric acid pumps with 50% of the nameplate capacity, which corresponded to a production output of 25 t/h of nitrobenzene. After 1 minute, the reaction product arrived in the phase separation apparatus and the acid water stripper was set to discharge of the acidic wastewater and the bottoms column of the distillation was set to product discharge of the nitrobenzene end product. The running of the production plant up to nameplate load, which is automated in a modern production plant, took another 1 hour.

Assessment of the Energy and Auxiliaries Required and Time Taken for the Running Down and Starting Up of the Plant Including the Cleaning Measure:

The total time taken for the measure was 15 hours. This applies if sufficient personnel is available and no technical difficulties occur. The time taken for the cleaning itself was 8 hours. For the shutdown, 2.5 hours were required. The startup took 4.5 hours.

Thus, a total of 775 tonnes of nitrobenzene production was lost. The steam consumption was 4.4 tonnes of 6 bar steam, 8 tonnes of 16 bar steam and 4.8 tonnes of 110 bar steam. In the running down of the plant and during the measure, no steam was consumed. The consumption of nitrogen for the running down was 550 m³ (STP) and for the startup of the plant was 100 m³ (STP). The consumption of condensate was 15.5 m³ (2 m³ for the purging of the heat exchanger and 13.5 m³ for the startup of the neutral wash). The consumption of power totaled 6130 kW. For the running down of the plant, 1100 kW were required for the TDZ, 180 kW for the nitration and 445 kW for the washes. For the startup of the plant, 4005 kW were required for the washes and 400 kW for the circulating sulfuric acid pumps. During the cleaning measure, no power was consumed.

Example 1: Brief Shutdown of the Production Plant with Circulation Mode in the Plant Sections Unaffected by the Cleaning Measure, Cleaning Measure and Restarting of the Plant The brief shutdown of the plant served for cleaning operations in the nitration region. For this purpose, the nitration region was run down completely and the other plant sections such as the washes, the distillation, and the acidic and alkaline wastewater workup were put in circulation mode. The energy supplies during the cleaning operations were switched off only in the nitration region (the vacuum remained on standby). After the cleaning operations, the plant was started up again, for which it was necessary to completely inertize, fill and heat up only the nitration region.

Procedure for the Complete Stoppage of the Nitration and Adjustment of the Remaining Plant Sections to Circulation Mode:

Firstly, the acid water workup was put in circulation mode by switching the discharge of the acidic wastewater into the wastewater channel back into the acid water reservoir tank by means of the bottoms pump of the stripper, which requires 10 kW/h. The steam to the acid water stripper was throttled from 1.2 t/h to 0.7 t/h of 6 bar steam and the feed of acid water from the acid water reservoir tank by means of the acid water pump, which requires 10 kW/h, into the acid water stripper was reduced from 20 m³ to 13 m³. The changeover of the acid water workup to circulation mode took place within 33 seconds by means of automation.

Next, the alkaline wastewater workup was put in circulation mode by switching the discharge of the alkaline wastewater of the thermal pressure decomposition (TDZ) into the wastewater channel back into the alkaline wastewater reservoir by means of the high-pressure pump of the TDZ, which requires 55 kW/h. The steam to the pressure decomposition was throttled from 0.32 t/h to 0.20 t/h of 110 bar steam and the feed of alkaline wastewater from the alkaline wastewater reservoir into the TDZ was reduced from 4.0 m³/h to 2.5 m³/h. The changeover of the TDZ to circulation mode took place within 5 minutes by means of automation, because the reduction of the feeding to the TDZ was effected manually.

At the same time, the stripper of the alkaline wastewater was put in circulation mode by interrupting the discharge of the alkaline wastewater into the TDZ and switching the alkaline wastewater back to the wastewater tank by means of the bottoms pump of the stripper, which requires 10 kW/h. The steam to the stripper for the alkaline wastewater was throttled from 0.4 t/h to 0.25 t/h of 6 bar steam, and the feed of alkaline wastewater from the wastewater tank into the stripper for the alkaline wastewater was reduced from 4 m³ to 2.5 m³ by means of the injection pump for the alkaline wastewater, which requires 10 kW/h. The changeover of the stripper for the alkaline wastewater to circulation mode took place within 27 seconds by means of automation.

Next, the washes and the distillation were put in circulation mode by switching the discharge of the nitrobenzene end product from the nitrobenzene column to the nitrobenzene storage tank over to the crude nitrobenzene tank by means of the bottoms pump of the column, which requires 24 kW/h. At the same time, the benzene-containing organic phase of the vapor phase separation apparatus was guided by means of natural efflux to the crude nitrobenzene tank. The aqueous phase of the vapor phase separation apparatus was disposed of via the acidic wash and the acidic wastewater workup. The vacuum system of the nitrobenzene column remained in operation. The circulation mode was established by running the contents of the crude nitrobenzene tank by means of delivery pumps through all the washes back to the nitrobenzene column. The crude nitro tank, the acidic wash, the alkaline wash and the 3 neutral washes each have a delivery pump, each of which requires 24 kW/h. The feed of crude nitrobenzene into the washes or distillation was reduced from 42 t/h to 27 t/h. The steam to the nitrobenzene column was throttled from 2.5 t/h to 1.6 t/h of 16 bar steam. The wash water for the neutral wash was reduced from 6.3 m³/h to 4.0 m³/h. The changeover of the washes and the distillation to circulation mode took place within 5 minutes by means of automation.

Lastly, the nitration was shut down by switching off the metering pumps for the input streams of benzene and nitric acid. The vapor from the flash evaporator was stopped 5 minutes after the benzene and nitric acid raw materials. The circulation of sulfuric acid continued for 1 hour until all organics were discharged from the nitration circuit consisting of nitrators, phase separation apparatus, flash evaporator and circulating sulfuric acid reservoir tank. Then the circulation of sulfuric acid at 100° C. was interrupted by switching off the circulation pump. The nitrators, the phase separation apparatus and the flash evaporator were left under standing sulfuric acid. The remaining circulating sulfuric acid was in the sulfuric acid reservoir tank. Simultaneously with the circulation pump, the vacuum pump to the flash evaporator was shut down and the vacuum was broken with 350 m³ (STP) of nitrogen. The nitration circuit was then at rest. The time taken for the shutdown was 2 hours.

The preparation (establishing circulation mode of washing, distillation, alkaline and acidic wastewater and the shutdown of the nitration) for the cleaning measure took a total of 2 hours and 11 minutes without purging and emptying of the apparatuses, pumps and pipelines.

Procedure for the Cleaning Measure:

The cleaning measure was conducted as described in example 1.

Procedure for the Restarting of the Plant:

The vacuum pump for the flash evaporator was put in operation beforehand. The phase separation apparatus and the cleaned benzene preheater were inertized with 100 m³ (STP) of nitrogen. The startup of the plant was started with the starting of the nitration, by starting the sulfuric acid circulation pump and running the sulfuric acid in circulation through the nitrator, phase separation apparatus, flash evaporator and sulfuric acid reservoir tank. In the flash evaporator, the vacuum had already been started, and then 2.4 t/h of 6 bar steam were applied, which heated the circulating sulfuric acid to starting temperature. This operation took 1 hour until the circulating sulfuric acid cooled down to 93° C. had been heated up to 100° C. Then the nitration was started by starting the benzene and nitric acid pumps at 50% of the nameplate capacity, which corresponded to a production output of 25 t/h of nitrobenzene. After 1 minute, the reaction product arrived in the phase separation apparatus, the acid water stripper was set to discharge of the acidic wastewater and the bottoms column of the distillation was set to product discharge of the nitrobenzene end product. At the same time, the stripper for the alkaline wastewater workup was switched to discharge to the TDZ, and the TDZ was switched from circulation mode to discharge into the wastewater channel. The running of the production plant up to nameplate load, which is automated in a modern production plant, took another 1 hour.

Assessment of the Energy Required and Time Taken for the Running Down and Starting Up of the Plant from Circulation Mode, Including the Cleaning Measure:

The total time taken for the measure was 11 hours and 12 minutes. This applies particularly if sufficient personnel is available and no technical difficulties occur. The time taken for the cleaning itself was 8 hours. The running down into circulation mode took 2 hours and 11 minutes. The startup from circulation mode took 1 hour and 1 minute.

In this way, a total of 585 tonnes of nitrobenzene production was lost. The steam consumption was 12 tonnes of 6 bar steam, 13 tonnes of 16 bar steam and 1.6 tonnes of 110 bar steam for the circulation mode. In the running down of the plant into circulation mode, no steam was consumed. The consumption of nitrogen for the running down into circulation mode was 350 m³ (STP) and for the startup of the plant from circulation mode was 100 m³ (STP). The consumption of condensate for the measure was 47 m³ (2 m³ for the purging of the heat exchanger and 45 m³ for the running down and startup and circulation mode of the washes). The consumption of power totaled 8525 kW. The running down of the plant consumed 1943 kW, the circulation mode during the cleaning measure consumed 5680 kW for the circulation mode and the startup of the plant consumed 905 kW of power.

Conclusion for the Complete Stoppage (Comparative Example 1) Versus Circulation Mode (Example 1) for the Cleaning Measure:

As a conclusion for the complete stoppage (comparative example 1) versus circulation mode (example 2) according to the present invention, it can be stated that the extra demand for power and condensate is more than compensated for by the lower consumption of nitrogen, but particularly by the higher availability of the plant, which is manifested by a higher production output. The steam consumption is about the same. The time saved for the cleaning measure is 3 hours and 48 minutes, which corresponds to an improved production output of 190 tonnes of nitrobenzene.

Comparative Example 2: Brief Shutdown of the Production Plant with Complete Stoppage of the Plant, Repair Measure and Restarting of the Plant Brief shutdown of the plant for a repair measure in the washing operation: For this purpose, the plant was run down completely, i.e. nitration, washes and distillation. The energy supplies were switched off during the repair measure. After the repair, the plant was started up again, for which it was necessary to inertize, fill and heat the entire plant.

Procedure for the Complete Stoppage of the Plant:

The plant was shut down as described in example 1. The complete stoppage again took two hours without purging and emptying of the apparatuses, pumps and pipelines, neglecting the running-down of the TDZ.

Procedure for the Repair Measure:

Sealing of leaky pipeline in the neutral wash: For this purpose, the pipeline affected in the downstream washing apparatus was blown clear with 10 m³ of nitrogen. Then the pipeline was purged with 2 m³ of condensate and emptied. Subsequently, the failed seal in the pipeline was replaced. The repair measure took a total of 1.5 hours. In modern automated production plants, the number of personnel required for the preparation for the repair, namely the purging of the pipeline, plays an important role. In this case, one additional production worker is required. Workmen for disassembly and assembly of the pipeline in order to replace the failed seal are likewise required.

Procedure for the Restarting of the Plant:

The vacuum pumps in the entire production plant were put in operation beforehand. Subsequently, the plant was restarted as described in comparative example 1. The plant had been started up again after 4.5 hours and could be run up to nameplate load.

Assessment of the Energy Required and Time Taken for the Running Down and Starting Up of the Plant, Including the Cleaning Measure:

The total time taken for the measure was 8.5 hours, since sufficient personnel were available and no technical difficulties occurred. The time taken for the repair itself was 1.5 hours. For the shutdown, 2.5 hours were required. The startup took 4.5 hours. Thus, a total of 450 tonnes of nitrobenzene production was lost. The steam consumption was 3.4 tonnes of 6 bar steam and 8 tonnes of 16 bar steam and 4.8 tonnes of 110 bar steam. In the running down of the plant, no steam was consumed. A total of 610 m³ (STP) of nitrogen were required, of which 550 m³ (STP) was for the running-down and 50 m³ (STP) for the restarting of the plant, and a further 10 m³ (STP) for the repair measure.

The consumption of condensate was 15.5 m³ (2 m³ for the purging of the pipeline and 13.5 m³ for the startup of the neutral wash). The consumption of power totaled 5470 kW. For the running down of the plant, 440 kW were required for the TDZ, 180 kW for the nitration and 445 kW for the washes. For the startup of the plant, 4005 kW were required for the washes and 400 kW for the circulating sulfuric acid pumps. During the repair measure, no power was consumed.

Example 2: Brief Shutdown of the Production Plant with Circulation Mode in the Plant Sections Unaffected by the Repair Measure, Repair Measure and Restarting of the Plant Brief shutdown of the plant for repair operations in the nitrobenzene wash: For this purpose, the washes and distillation were run down completely. The other plant sections such as the nitration and the acidic and alkaline wastewater workup were put in circulation mode. The energy supplies during the repair operations were switched off only in the wash and the distillation (vacuum remained on standby). After the repair, the plant was restarted.

Procedure for the Complete Stoppage of the Washes and Distillation and Adjustment of the Remaining Plant Sections to Circulation Mode:

Firstly, the acid water workup was put in circulation mode by switching the discharge of the acidic wastewater into the wastewater channel back into the acid water reservoir tank by means of the bottoms pump of the stripper, which requires 10 kW/h. The steam to the acid water stripper was throttled from 1.2 t/h to 0.7 t/h of 6 bar steam and the feed of acid water from the acid water reservoir tank by means of the acid water pump, which requires 10 kW/h, into the acid water stripper was reduced from 20 m³ to 13 m³. The changeover of the acid water workup to circulation mode took place within 29 seconds by means of automation.

Next, the alkaline wastewater workup was put in circulation mode by switching the discharge of the alkaline wastewater of the thermal pressure decomposition (TDZ) into the wastewater channel back into the alkaline wastewater reservoir by means of the high-pressure pump of the TDZ, which requires 55 kW/h. The steam to the pressure decomposition was throttled from 0.32 t/h to 0.20 t/h of 110 bar steam and the feed of alkaline wastewater from the alkaline wastewater reservoir into the TDZ was reduced from 4.0 m³/h to 2.5 m³/h. The changeover of the TDZ to circulation mode took place within 5 minutes by means of automation, because the reduction of the feeding to the TDZ was effected manually.

At the same time, the stripper of the alkaline wastewater was put in circulation mode by interrupting the discharge of the alkaline wastewater into the TDZ and switching the alkaline wastewater back to the wastewater tank by means of the bottoms pump of the stripper, which requires 10 kW/h. The steam to the stripper for the alkaline wastewater was throttled from 0.4 t/h to 0.25 t/h of 6 bar steam, and the feed of alkaline wastewater from the reservoir tank into the stripper for the alkaline wastewater was reduced from 4 m³ to 2.5 m³ by means of the injection pump for the alkaline wastewater, which requires 10 kW/h. The changeover of the stripper for the alkaline wastewater to circulation mode took place within 31 seconds by means of automation.

Next, the feedstocks to the nitration were stopped. The metering pumps for the input streams of benzene and nitric acid were switched off. The circulating sulfuric acid continued to circulate at 100° C. through the nitrators, the phase separation apparatus, flash evaporator and circulating sulfuric acid reservoir tank. The flash evaporator required 0.3 t/h of 6 bar steam. The time taken was 1 minute.

Lastly, the washes were shut down by interrupting the crude nitrobenzene feed from the crude nitrobenzene tank to the acidic wash. The crude nitrobenzene pathway through the acidic, alkaline and neutral wash was stopped by stopping the delivery pumps for the crude nitrobenzene upstream of the respective washes. The washes were at 48° C. and remained filled with crude nitrobenzene. At the same time, the acidic, alkaline and neutral wash water pathway was stopped by switching off the respective pumps. The time taken was 5 minutes.

Then the distillation was shut down by interrupting the feed of crude nitrobenzene and taking away the steam to the distillation column Immediately thereafter, the product discharge was interrupted by switching off the bottoms pump and the return stream at the top of the column was stopped by stopping the benzene pump. The vacuum pump continued to run. The time taken was 5 minutes.

The preparation (establishment of circulation mode in the nitration and the alkaline and acidic wastewater workup and the shutdown of the washes and distillation) for the repair measure took a total of 11 minutes without purging and emptying of the apparatuses, pumps and pipelines.

Procedure for the Repair Measure:

The repair measure was conducted as described in comparative example 2. The time taken was again 1.5 hours. The steam consumption during circulation mode was 1.6 tonnes of 6 bar steam and 0.4 tonne of 110 bar steam. 400 kW of power were required for the operation of the vacuum pump and sulfuric acid circulation pump during circulation mode.

Procedure for the Restarting of the Plant:

Firstly, the washes were started by starting the crude nitrobenzene pump to put the crude nitrobenzene supply from the crude nitrobenzene tank to the acidic wash in operation. Thereafter, the acidic, alkaline and neutral wash water pathway was started by switching on the respective pumps. Then the crude nitrobenzene pathway through the acidic, alkaline and neutral wash was started by switching on the delivery pumps for the crude nitrobenzene upstream of the respective washes. The washing apparatuses that were filled with crude nitrobenzene and wash water were at 45° C. and were gradually warmed back to 48° C. after the production plant had been started.

Once the last stage of the neutral wash had been put in operation by feeding in 3° t/h of condensate, the distillation was started by running crude nitrobenzene at 45° C. from the last neutral wash to the distillation column. Thereafter, the bottoms pump of the column was started and crude nitrobenzene was run to the crude nitrobenzene tank. Then the distillation column was supplied with 2 t/h of 16 bar steam and heated up to 170° C. At 50° C. at the top of the column, the reflux was put in operation by starting the benzene pump. The washes and the distillation were ready for restarting of the production plant after 1 hour.

Then the nitration was started by starting the benzene and nitric acid pumps at 50% of the nameplate capacity, which corresponded to a production output of 25 t/h of nitrobenzene. After 1 minute, the reaction product arrived in the phase separation apparatus, the acid water stripper was set to discharge of the acidic wastewater and the bottoms column of the distillation was set to product discharge of the nitrobenzene end product. At the same time, the stripper for the alkaline wastewater workup was switched to discharge to the TDZ, and the TDZ was switched from circulation mode to discharge into the wastewater channel. The running-up of the production plant to nameplate load took another 1 hour.

Assessment of the Energy Required and Time Taken for the Running Down and Starting Up of the Plant from Circulation Mode, Including the Repair Measure:

The total time taken for the measure was 3 hours and 41 minutes. The time taken for the repair itself was 1.5 hours. The running-down into circulation mode took 11 minutes. The startup from circulation mode took 1 hour and 1 minute.

Thus, a total of 165 tonnes of nitrobenzene production was lost. The steam consumption was 1.6 tonnes of 6 bar steam, 2 tonnes of 16 bar steam and 0.8 tonne of 110 bar steam. In the running down of the plant into circulation mode, no steam was consumed. 10 m$^3$ (STP) of nitrogen were required for the repair measure and 50 m$^3$ (STP) of nitrogen for the restarting of the plant. The consumption of condensate was 7 m$^3$ (2 m$^3$ for the purging of the pipeline and 5 m$^3$ for the running-down and startup of the neutral wash). The consumption of power totaled 1593 kW. The running-down of the plant consumed 178 kW for the running-down of the nitration into circulation mode, 510 kW for the circulation mode during the cleaning measure and 905 kW of power for the startup of the plant.

Conclusion for the Complete Stoppage (Comparative Example 2) Versus Circulation Mode (Example 2) for the Repair Measure:

As a conclusion for the complete stoppage (comparative example 2) versus circulation mode (example 2) according to the present invention, it can be stated that smaller amounts of steam, power, nitrogen and condensate were consumed in circulation mode and, on top of that, the availability of the plant, which is manifested by a higher production output, was distinctly better. The time saved for the repair measure was 5 hours and 48 minutes, which corresponds to an improved production output of 290 tonnes of nitrobenzene.

General Conditions for the Preparation of MDA in a Run-In Production Plant

In a continuous reaction process (step a)), 24.3 t/h of input aniline (containing 90% by mass of aniline) and 9.9 t/h of 32% aqueous formaldehyde solution (formalin) (molar ratio of aniline to formaldehyde 2.1:1) were mixed and converted to the aminal at 90° C. and 1.4 bar absolute in a stirred reaction tank. The reaction tank was provided with a cooler having a cooling circuit pump. The reaction mixture leaving the reaction tank was guided into a phase separation apparatus (aminal separator) (step b)). After the phase separation to remove the aqueous phase, the organic phase was admixed in a mixing nozzle with 30% aqueous hydrochloric acid (protonation level 10%, i.e. 0.1 mol of HCl is added per mole of amino groups) and run into the first rearrangement reactor. The rearrangement reaction was conducted in a reactor cascade at 45° C. to 165° C. (step c)). On completion of reaction, the reaction mixture obtained was admixed with 32% sodium hydroxide solution in a molar ratio of 1.1:1 sodium hydroxide to HCl and reacted in a stirred neutralization vessel (step d)). The temperature was 115° C. and the absolute pressure 1.4 bar. The neutralized reaction mixture was then separated in a neutralization separator into an aqueous lower phase, which was guided to a wastewater collecting vessel, and an organic phase (step e)). The organic upper phase was directed to the washing operation and washed in a stirred wash vessel with condensate and/or water from the sidestream of the wastewater column (aniline/water mixture) (step f)). After the wash water had been removed in a wash water separator (step g)), the crude MDA thus obtained was freed of water and aniline by distillation, giving 17 t/h of MDA as bottom product (step h)).

Comparative Example 3: Running the Plant Down to Complete Shutdown for a Repair and Restarting of the Plant Firstly, the entire production plant from example 1 was brought to a production load of 10 t/h of MDA, in order to be able to clear the plant very rapidly by purging with aniline, but also to allow a minimum amount of waste product, such as aniline, crude MDA and wastewater, all of which have to be reprocessed, to occur.

The shutdown of the plant was commenced with the stopping of the input stream of formaldehyde into the aminal reactor. For this purpose, the formaldehyde pump was stopped and the formaldehyde pathway from the formaldehyde reservoir tank was freed of formaldehyde by purging with water for 10 minutes. Then the aminal section of the plant was diluted with amount of aniline for 3 hours, with depletion of residual formaldehyde by reaction to give aminal and purging thereof out of the aminal reactor. During the purge operation, the amount of aniline was increased such that balancing for the now absent amount of aminal took place, in order to assure a homogeneous mass flow rate, and not to have to reduce the levels in the downstream apparatuses. The heat of reaction no longer arose after the formalin supply had been stopped, and the aminal reactor cooled down to 67° C. After 3 hours, the aniline supply was stopped, the cooling circuit was shut down, and the aminal cooler, the aminal pump and the stirred aminal vessel were successively emptied of residues into the aminal separator. The pressure in the aminal vessel remained at 1.4 bar absolute during the purge operation. The aminal separator was then likewise emptied of residues by running the purge aniline and the residual water above the aniline into the first rearrangement reactor. The aminal section was then at rest. The running-down took a total of 5 hours.

Next, the reactor cascade of the rearrangement reaction was run down. Here, at the early stage of 2 hours after commencement of the shutdown of the aminal section of the plant, the reactor cascade was charged with more steam in order to compensate for the lost heat of reaction. The temperatures in the reactor cascade were left at 45° C. to 165° C. The running-down of the reactor cascade was commenced with the ending of the metered addition of 30% aqueous hydrochloric acid into the mixing nozzle upstream of the first rearrangement reactor at the time when the emptying of residues from the aminal separator was started. Then the reactors of the reactor cascade were successively run empty for neutralization. Steam and vacuum were stopped once the last rearrangement tank was empty. Then the reactor cascade of the rearrangement reaction was at rest. The running-down took a total of 3 hours.

Thereafter, the neutralization was put out of operation by running 32% sodium hydroxide solution into the stirred neutralization vessel for 10 minutes longer than diluted reaction mixture from the reactor cascade of the rearrangement reaction. Then the contents of the stirred neutralization vessel and separator were emptied of residues into an alkaline discharge vessel. The absolute pressure remained at 1.4 bar. The neutralization was then at rest. The running-down operation with emptying of residues took 2 hours.

Next, the wash was put out of operation by first passing condensate and/or water from the sidestream of the wastewater column (aniline/water mixture) in a circuit to the stirred wash vessel. The stirrer of the wash vessel was switched off and the contents of the wash vessel were emptied into the wash water separator. The contents of the wash water separator were emptied into the distillation reservoir. The wash was then at rest. The running-down operation took 2 hours.

Lastly, the distillation was shut down by, after the emptying of residues from the wash, switching the complete distillation to circulation mode, with dilution of the crude MDA present in the distillation with 6 t/h of aniline from the aniline reservoir tank. The steam to the distillation was stopped. The distillation was run "cold" by means of the vacuum that still existed over the course of 4 hours. Subsequently, the vacuum was stopped and the contents of the complete distillation (distillation reservoir, heat exchanger, preliminary distillation column with condensation system, MDA column with bottoms withdrawal, steam generator) were emptied into the alkaline discharge vessel. Then the distillation was at rest, and the running-down operation took 4 hours.

During the cold running of the distillation, the wastewater workup was taken out of operation by first emptying the aniline/water mixture from the wastewater extraction, which consisted of wastewater collecting vessel, wastewater heater and aniline separating vessel, into the wastewater tank. The wastewater distillation, consisting of a heat exchanger, a process wastewater distillation column with condensation system, a process wastewater cooler and a sidestream reservoir of the process wastewater distillation column, was shut down by stopping the steam to the wastewater distillation and then emptying the contents of the wastewater distillation into the wastewater tank.

Now the complete MDA plant was at rest, and had also been completely emptied at this time. The plant pressure was adjusted to ambient pressure by taking all pressure-retaining devices in the plant out of operation. The residual emptying valves of all plant sections were opened once again in order to discharge residual substances from the plant. The complete shutdown with emptying of all apparatuses, pumps and pipelines took a total of 24 hours.

Consumption:

20 m³ (STP) of nitrogen to break the vacuum and 500 kW of power for the circulation mode of the distillation were consumed. In addition, an elevated steam demand arose in the reactor cascade of the rearrangement reaction of 5 tonnes of 6 bar steam and 5 tonnes of 16 bar steam. In addition, 10 tonnes of purge aniline arose, which had to be treated prior to use in the aminal reaction.

Performance of a One-Day Maintenance Measure

It was necessary to replace a defective stirrer unit in the wash vessel.

Preparation for Restarting of the Plant

All plant sections were first brought into circulation mode. The restarting of the plant commenced with the parallel initiation of all circuits in the overall plant. Firstly, the plant sections were charged with aniline and/or auxiliaries such as HCl or NaOH.

Charging of the Aminal Section and Establishment of Circulation Mode:

Firstly, the aniline reservoir was charged with fresh aniline from the aniline reservoir tank. Then the empty aminal reactor was charged with aniline until aniline ran over through the siphon into the aminal separator. Once the aminal separator was half-filled with aniline, the aniline stream to the aminal reactor was stopped and the aminal circulation mode was implemented by means of the pump from the aminal separator. 4 t/h of aniline were then pumped in a circuit from the aminal separator through the aminal reactor. Time taken: 3 hours.

Charging of the Reactor Cascade of the Rearrangement Reaction and Establishment of Circulation Mode:

The first rearrangement reactor was charged with fresh aniline from the aniline reservoir tank up to a level of 60%. Then the aniline stream was stopped and the first rearrangement reactor was pumped in a circuit with 24 t/h of fresh aniline by means of the discharge pump. The remaining rearrangement reactors of the reactor cascade were charged from the acidic discharge vessel with a mixture that consisted of aniline, hydrochloric acid and traces of crude MDA, and the rearrangement circulation mode was set in motion by means of the pumps of the rearrangement reactors from the last rearrangement reactor to the second rearrangement reactor. 10 t/h of the mixture from the acidic discharge vessel were then pumped in a circuit and heated up to 100° C. with steam. The remaining 15 tonnes of the mixture from the acidic discharge vessel had to be added later in the course of production, but this means a variation in the bicyclic content of the end product. Time taken: 8 hours.

Charging of the Neutralization and Establishment of Circulation Mode:

2 tonnes of 32% sodium hydroxide solution from the sodium hydroxide solution reservoir tank and 8 tonnes of condensate from the condensate reservoir vessel were run into the stirred neutralization vessel. The stirred neutralization vessel was then filled, and 2 tonnes of the dilute sodium hydroxide solution were passed through the siphon into the neutralization separator. By means of the pump of the neutralization separator, the circulation mode was set in motion by pumping the dilute sodium hydroxide solution from the neutralization separator into the stirred neutralization vessel. 4 t/h of dilute sodium hydroxide solution were then pumped in a circuit from the neutralization separator through the stirred neutralization vessel. Time taken: 4 hours.

The Washing Operation was not Charged and was not Put in Circulation Mode Either:

The stirred vessel of the washing operation and the connected separator remained empty until the plant was started up.

Charging of the Distillation and Establishment of Circulation Mode:

The distillation reservoir was charged with fresh aniline from the aniline reservoir tank up to a fill level of 60%. From the distillation reservoir, the complete distillation consisting of heat exchanger, preliminary distillation column with condensation system, MDA column with bottoms withdrawal and steam generator was then charged with fresh aniline, fresh aniline was stopped, and 10 t/h of fresh aniline were run in a circuit through the preliminary distillation column and MDA column Subsequently, the vacuum of the distillation was put in operation and the entire distillation was heated to 100° C. with steam. Time taken: 5 hours.

Charging of the Wastewater Treatment and Establishment of Circulation Mode:

Wastewater was pumped from the wastewater tank into the wastewater collecting vessel. Then wastewater was conveyed from the wastewater collecting vessel into the wastewater heater and aniline separating vessel. Fresh aniline from the aniline reservoir tank was then applied to the wastewater heater, then the wastewater heater was heated up to 90° C. and the mixture of fresh aniline and wastewater from the wastewater heater was passed in a circuit through the aniline separating vessel and the wastewater collecting vessel. The wastewater distillation remained out of operation until the plant was started up. Time taken: 5 hours.

A total of 15 hours are required to put the entire plant in circulation mode, as described, because parts of the plant were being charged in parallel. For this purpose, 50 tonnes of 16 bar of steam and 9500 kW of power for operation of the motors were required.

Restarting of the Plant

The plant was running as described in the preparations for recommissioning of the plant in circulation in the individual operating segments, meaning that it was heated, stirrers were in operation, blanketing pressure with nitrogen and reduced pressure was available in the areas required. Feedstocks and auxiliaries were ready for use.

Startup of the Distillation with Vacuum System:

The distillation with vacuum system was in circulation mode. The vacuum system of the preliminary distillation column and MDA column was put in operation and set to 120 mbar absolute. Then the 16 bar steam (consumption: 40 tonnes) to the preliminary distillation column and the 110 bar steam (consumption: 10 tonnes) to the MDA column were opened and the columns were heated up. The temperature in the preliminary distillation column was 190° C. and that in the MDA column 225° C. The aniline needed for distillation was fed from the aniline reservoir into the pump reservoir of the distillation for the period of circulation mode. The steam generator was in operation. The operating segment of the distillation was then ready to accept crude MDA. Time taken: 3 hours.

Startup of the Aminal Reaction:

30 minutes before the distillation was ready to accept crude MDA, the aminal preparation was started by opening aniline to the aminal reactor and, 10 minutes later, starting the formalin flow. At the same time, the path of the organic phase at 90° C. from the aminal separator to the first reactor of the rearrangement reaction was opened and the temperature in the first rearrangement reactor was lowered to 50° C. by means of reduced pressure. It was now possible to start the acidic catalysis of the rearrangement reaction with hydrochloric acid. The aminal water obtained in the aminal separator was sent to the wastewater workup. The operating segment of the aminal reaction had then been started and aminal solution was passed to the rearrangement reaction. Time taken: 15 minutes.

Startup of the Rearrangement Reaction:

Once the hydrochloric acid stream had been put in operation and the temperature in the first rearrangement reactor had been attained, the further rearrangement reactors and delay towers of the reactor cascade were heated up to 60° C. up to the last reactor to 165° C. (consumption: 60 tonnes of 16 bar steam). The operating segment of the rearrangement reaction had then been started and the condensation solution consisting of MDA, aniline and hydrochloric acid (crude MDA) was neutralized next. Time taken: 10 minutes.

Startup of the Neutralization:

The sodium hydroxide solution metering unit was put in operation by running sodium hydroxide solution and wash water to the stirred neutralization vessel. 10 minutes later, the route of the acidic condensation solution from the rearrangement reaction was opened up. The operating segment of the neutralization had then been started and it was possible to wash crude MDA. Time taken: 10 minutes.

Startup of the Wash:

Neutralized crude MDA at 116° C. arrived in the MDA washer and was washed with condensate. The wash water addition, consisting of condensate and/or the sidestream from the process wastewater column, was started. The operating segment of the wash had then been started. Crude MDA left the phase separation apparatus and was passed to the distillation. Time taken: 5 minutes.

Startup of the Wastewater Workup:

As soon as the neutralization and wash were running, the wastewater workup was started by putting the wastewater extraction and wastewater distillation in operation. For this purpose, the wastewater obtained from the process steps described above (neutralization, wash and distillation) that arrived in the wastewater collecting vessel was run by means of a pump through the process wastewater heater into the aniline separation vessel. The extracted wastewater passed from there into the wastewater distillation. The wastewater distillation was heated to 107° C. with 20 tonnes of 6 bar steam, and the wastewater left the production plant. Time taken: 2 hours.

The complete MDA plant was now running at a reduced load of 10 t/h of MDA and could then be run up to the desired target production. Overall, 10 hours were required to put the overall plant in operation from circulation mode as described and to discharge first end product into the MDA tank. For this purpose, 100 tonnes of 16 bar steam, 10 tonnes of 110 bar steam and 20 tonnes of 6 bar steam, and also 6315 kW of power to operate the motors, were required.

It was absolutely necessary to start up the production plant at reduced load, since the temperature profiles required for aminal and rearrangement reaction, neutralization, washing and wastewater workup and distillation were otherwise not available quickly enough. This would lead to incomplete reactions, increased by-products and inadequate workup of the product.

Conclusion:

The time taken for the complete production shutdown (running down, measure and starting up) encompassed 73 hours.

The energy consumption for the purpose (running down, measure and starting up) was 15 815 kW of power, 105 tonnes of 16 bar steam, 10 tonnes of 110 bar steam and 25 tonnes of 6 bar steam. In addition, auxiliaries were consumed in the form of 20 m³ (STP) of nitrogen to break the vacuum.

Example 3: Bring Plant into Circulation Mode, Repair in the Wash Operation, Run Plant Up Again from Circulation Mode Firstly, the entire production plant was brought to the optimal production load of 10 t/h of MDA as in comparative example 3, in order then to bring the entire plant into circulation mode.

The actual adjustment of the plant to circulation mode began with the stopping of the input stream of formalin into the aminal reactor. For this purpose, the formaldehyde pump was stopped and the formaldehyde pathway from the formaldehyde reservoir tank was freed of formaldehyde by purging with water for 10 minutes. Then the aminal section of the plant was diluted with aniline for 30 minutes, with continued depletion of formaldehyde by reaction to give aminal and dilution of the aminal solution. During the purge operation, the amount of aniline was increased such that balancing for the now absent amount of aminal took place, in order to assure a homogeneous mass flow rate, and not to have to reduce the levels in the downstream apparatuses.

The heat of reaction no longer arose after the formaldehyde supply had been stopped, and the aminal reactor cooled down to 67° C. After 30 minutes, the aniline supply was stopped and the aminal section of the plant was put in circulation mode by pumping the aniline-diluted aminal in uncooled form from the aminal reactor through the siphon into the aminal separator and thence back in circulation to the aminal reactor. The pressure in the aminal vessel remained at 1.4 bar absolute during the circulation mode. The adjustment of the aminal section of the plant to circulation mode took a total of 1 hour.

Next, the reactor cascade of the rearrangement reaction was put in circulation mode by first stopping the hydrochloric acid stream and then the aminal stream. It was then possible to pump the condensation solution consisting of MDA, aniline and hydrochloric acid without heating from the last rearrangement reactor into the first rearrangement reactor and through the reactor cascade in circulation. The adjustment of the rearrangement section of the plant to circulation mode took a total of 1 hour.

Next, the neutralization was put in circulation mode by first stopping the acidic condensation solution that came from the rearrangement reaction, and 10 minutes later the 32% sodium hydroxide solution and the wash water. Then the contents of the neutralization separator were pumped by means of the circulation pump from the neutralization separator into the stirred neutralization vessel via the siphon back into the neutralization separator. The circulation mode was thus at rest. The absolute pressure in the neutralization remained at 1.4 bar absolute. The adjustment of the neutralization section of the plant to circulation mode took a total of 40 minutes.

Next, the wash was shut down by closing the addition of wash water consisting of condensate to the stirred wash vessel. The stirrer of the wash vessel was switched off. In order to prepare for the repair measure in the wash operation, the contents of the wash vessel were emptied into the wash water separator. The contents of the wash water separator were emptied into the distillation reservoir. The wash was then at rest. The running-down operation took 2 hours.

Lastly, the distillation was put in circulation mode by, after the emptying of residues from the wash, diluting the crude MDA present in the distillation with 6 t/h of aniline from the aniline reservoir tank. No further crude MDA arrived in the pump reservoir of the distillation. The bottoms effluent from the MDA column was put through the steam generator and the heat exchanger back to the pump reservoir of the distillation, and hence run through the pump reservoir, the heat exchanger, the preliminary distillation column and back into the bottom of the MDA column in circulation. Then it was possible to stop the steam to the preliminary distillation column and MDA column. Subsequently, it was possible to shut down the vacuum system of the two columns. The adjustment of the distillation section of the plant to circulation mode took a total of 3 hours.

Lastly, the wastewater workup was put in circulation mode once no further process water occurred. The wastewater extraction, consisting of wastewater collection vessel, wastewater heater and aniline separation vessel, was put in circulation mode by switching the effluent from the aniline separation vessel to the wastewater collection vessel and pumping it by means of a pump through the process wastewater heater into the aniline separation vessel in circulation. It was possible to operate the circulation mode without heating for an indefinite period. The wastewater distillation, consisting of a heat exchanger, a process wastewater distillation column with condensation system, a process wastewater cooler and a sidestream reservoir of the process wastewater distillation column, was shut down by stopping the steam to the column. No circulation mode of the wastewater distillation was intended here.

Now the complete MDA plant apart from the wash was running in circulation mode. The establishment of circulation mode took 6 hours.

Consumption:

20 $m^3$ (STP) of nitrogen to break the vacuum, and 3825 kW of power to bring the plant into circulation mode, occurrence of 10 tonnes of purge aniline in the distillation, which had to be processed prior to use in the aminal reaction.

Performance of a One-Day Maintenance Measure

A defective sightglass and a leaky seal had to be changed in the wash vessel. The circulation mode during the measure required 15 300 kW of power. Only a little steam was consumed in order to keep the circuits to temperature (12 tonnes of 16 bar steam).

Preparation for Restarting of the Plant

There were no preparations for restarting of the plant, since all plant sections were already running in circulation mode. Therefore, there was also no filling of the plant sections with aniline and/or auxiliaries such as hydrochloric acid or sodium hydroxide solution.

Restarting of the Plant

The plant was running in circulation in the individual operating segments as described above in the preparations for restarting of the plant. Feedstocks and auxiliaries were ready, the plant sections had been heated up, stirrers were in operation, blanketing pressure of nitrogen was available in the required regions, and vacuum was likewise available.

The restarting of the plant was conducted as described in comparative example 3. The complete MDA plant was now running at a reduced load of 10 t/h of MDA and could then be run up to the desired target production. Overall, 10 hours were again required to put the overall plant in operation from circulation mode as described and to discharge first end product into the MDA tank. For this purpose, 100 tonnes of 16 bar steam, 10 tonnes of 110 bar steam and 20 tonnes of 6 bar steam, and also 6315 kW of power to operate the motors, were likewise required.

The time taken for the entire operation (running down, execution of the measure and startup) was 40 hours. Thus, given a nameplate load of 380 tonnes per day, there was extra production of 522.5 tonnes of MDA compared to comparative example 3.

The energy consumption for the entire operation (running down, measure and startup) comprised 25 500 kW of power, 112 tonnes of 16 bar steam, 10 tonnes of 110 bar steam and 25 tonnes of 6 bar steam, and a consumption of auxiliaries in the form of 20 $m^3$ (STP) of nitrogen to break the vacuum.

Conclusion: In inventive example 3 with circulation mode, 7 tonnes of 16 bar steam and 9685 kW of power more are consumed than in the case of a complete shutdown of the plant as in comparative example 3. On the other hand, greatly improved productivity of the plant is found, since more than 500 tonnes more of MDA were producible because of the shorter time taken for the whole operation (running down, measure and startup).

The invention claimed is:

1. A process for preparing a chemical product or a chemical composition, comprising:
   (I) reacting at least one substrate in a reactor to form a polyphasic reaction mixture comprising at least one chemical product or a chemical composition, in which the mass flow of said at least one substrate being introduced into the reactor is $m_1$, wherein the reactor may be part of a reactor line in which two or more reactors are operated in parallel;

(II) working up the polyphasic reaction mixture obtained in step (I) in a workup apparatus to obtain a crude product, which is an organic phase comprising the desired chemical product or chemical composition, and at least one secondary stream, which is an aqueous phase and/or a gas phase that is separated from the crude product;

(III) optionally, purifying the crude product obtained in step (II) in at least one purifying apparatus, in which at least one secondary stream is removed to obtain a purified end product alongside the at least one secondary stream removed from the purified end product;

(IV) optionally, working up the at least one secondary stream obtained in step (II) in a workup unit; and (V) if (III) is performed, optionally working up the at least one secondary stream obtained in step (III) in a workup unit, comprising shutting down one or more plant sections from (I) to (V), including interrupting the formation of further chemical product or further product composition by reducing the mass flow $m_1$ in (I) to zero and stopping said one or more plant sections, conducting an inspection, repair, maintenance or cleaning measure in said one or more plant sections that have been shut down, and, operating at least one of the plant sections that has not been shut down in circulation mode in which an output stream of said at least one plant section operating in circulation mode is used as an input stream for said at least one plant section operating in circulation mode or an upstream plant section that has not been shut down.

2. The process as claimed in claim 1, comprising (I) to (III).

3. The process as claimed in claim 2, additionally comprising (IV) and (V).

4. The process as claimed in claim 3, wherein every plant section that has not been shut down is operated in circulation mode.

5. The process as claimed in claim 1, wherein at least two substrates are reacted in the reactor from (I) and the second substrate is introduced into the reactor from (I) with a mass flow $m_2$.

6. The process as claimed in claim 1, further comprising (Ia), wherein at least one third substrate is reacted with the product of the reaction from (I) in the reactor from (I) or in a further reactor, and the at least one third substrate is introduced into the at least one reactor from (Ia) with a mass flow $m_3$.

7. The process as claimed in claim 1, wherein the chemical product is a polycarbonate or one of its precursors, an isocyanate or one of its precursors, an active pharmaceutical ingredient, an olefin, aromatic or polyolefin.

8. A method of operating a plant for preparing a chemical product or a product composition during a shutdown of the preparation process, in which the plant comprises plant sections of:

(I) a reactor for converting at least one substrate to a polyphasic product mixture comprising the desired chemical product or product composition, wherein the reactor may be part of a reactor line in which two or more reactors are operated in parallel, (II) a workup apparatus for obtaining a crude product, which is an organic phase comprising the desired chemical product or chemical composition, from the polyphasic product mixture obtained in said reactor alongside at least one secondary stream, which is an aqueous phase and/or a gas phase separated from the crude product, (III) optionally, a purifying apparatus for purifying the crude product obtained in said workup apparatus to give a purified end product with removal of at least one secondary stream separated from the purified end product, (IV) optionally, a workup unit for workup of the at least one secondary stream obtained in said workup apparatus, and (V) if the purifying apparatus is present, optionally a workup unit for workup of the at least one secondary stream obtained in said purifying apparatus, wherein the method comprises:

(i) interrupting the formation of further chemical product or further product composition by stopping the supply of said at least one substrate into any reactor (I), (ii) operating at least one of the plant sections in circulation mode, in which an output stream of said at feast one plant section operating in circulation mode is used as an input stream for said at least one plant section operating in circulation mode or as an input steam for an upstream plant section;

and (iii) shutting down at least one of the plant sections (I) through (V) that is not operating in circulation mode by stoppage of said plant section that is not operating in circular mode and conducting an inspection, repair, maintenance or cleaning measure in said plant section.

9. The method as claimed in claim 8, further comprising:

(iv) optionally opening the at least one plant section shut down in (iii);

(v) performing a maintenance, cleaning, inspection and/or repair measure in the plant section shut down in (iii);

(vi) if (iv) is performed, closing and optionally inertizing the at least one plant section from (v);

(vii) starting up the at least one plant section from (vi); and (viii) starting the supply of the at least one substrate to the reactor (I).

* * * * *